United States Patent
Itami et al.

(10) Patent No.: US 9,029,551 B2
(45) Date of Patent: May 12, 2015

(54) CARBON NANORING, METHOD FOR PRODUCING SAME, COMPOUND SUITABLE AS STARTING MATERIAL FOR PRODUCING THE CARBON NANORING, AND METHOD FOR PRODUCING THE COMPOUND

(75) Inventors: Kenichiro Itami, Nagoya (JP); Yasutomo Segawa, Nagoya (JP); Haruka Omachi, Nagoya (JP); Sanae Matsuura, Nagoya (JP); Katsuma Matsui, Nagoya (JP)

(73) Assignee: National University Corporation Nagoya University, Nagoya-shi (JP)

( * ) Notice: Subject to any disclaimer, the term of this patent is extended or adjusted under 35 U.S.C. 154(b) by 0 days.

(21) Appl. No.: 13/578,592

(22) PCT Filed: Feb. 10, 2011

(86) PCT No.: PCT/JP2011/052948
§ 371 (c)(1), (2), (4) Date: Oct. 23, 2012

(87) PCT Pub. No.: WO2011/099588
PCT Pub. Date: Aug. 18, 2011

(65) Prior Publication Data
US 2013/0041155 A1 Feb. 14, 2013

(30) Foreign Application Priority Data

Feb. 12, 2010 (JP) ................................. 2010-029490
Sep. 1, 2010 (JP) ................................. 2010-196174

(51) Int. Cl.
| | |
|---|---|
| C07D 213/26 | (2006.01) |
| C07C 41/30 | (2006.01) |
| C07C 15/20 | (2006.01) |
| C07C 43/188 | (2006.01) |
| C07D 471/22 | (2006.01) |
| C09K 11/06 | (2006.01) |
| C07D 487/22 | (2006.01) |

(52) U.S. Cl.
CPC ................. *C07C 41/30* (2013.01); *C07C 15/20* (2013.01); *C07C 43/188* (2013.01); *C07C 2101/14* (2013.01); *C07C 2103/90* (2013.01); *C07D 471/22* (2013.01); *C09K 11/06* (2013.01); *C09K 2211/1007* (2013.01); *C09K 2211/1029* (2013.01); *C07D 487/22* (2013.01)

(58) Field of Classification Search
None
See application file for complete search history.

(56) References Cited

PUBLICATIONS

CAPLUS 2010:202.*
Bachrach, S J Org Chem 2010 vol. 75 pp. 6595-6604.*
Wong, Bryan, "Optoelectronic Properties of Carbon Nanorings: Excitonic Effects from Time-Dependent Density Functional Theory," J. of Phys. Chem. C, 2009, vol. 113, No. 52, pp. 21921-21927.
Jasti et al., "Synthesis, Characterization, and Theory of [9]-, [12]-, and [18] Cycloparaphenylene: Carbon Nanohoop Structures," J. Am. Chem. Soc., 2008, vol. 130, No. 52, pp. 17646-17647.
Borman, Stu, "Nanotube Building Block Created," Chemical & Engineering News, 2008, vol. 86, No. 51, p. 9.
Omachi et al. "A Synthesis of [12]Cycloparaphenylene," Symp Organomet Jpn, 2009, vol. 58th, p. 62, Lecture No. P2A-15.
Takaba et al., "Selective Synthesis of [12]Cycloparaphenylene," Angew. Chem. Int. Ed., 2009, Vo.48, No. 33, pp. 6112-6116.
Dai 21 Kai Ban'yu Sapporo Symposium, 2009, pp. 3-11.
Omachi et al., "A Modular and Size-Selective Synthesis of [n]Cycloparaphenylenes: A Step toward the Selective Synthesis of [n,n] Single-Walled Carbon Nanotubes," Angew. Chem. Int. Ed., 2010, Vo.49, pp. 10202-10205.
International Search Report dated Apr. 19, 2011, issued for PCT/JP2011/052948.

* cited by examiner

*Primary Examiner* — Heidi Reese
(74) *Attorney, Agent, or Firm* — Locke Lord LLP; James E. Armstrong, IV; Nicholas J. DiCeglie, Jr.

(57) ABSTRACT

This invention provides: a compound for accurately forming a carbon nanoring that contains a specific number of organic rings and has a definite diameter; a method for producing the compound; a method for efficiently producing a carbon nanoring; and a cycloparaphenylene obtained by the production method. The carbon nanoring of the present invention is a compound obtained by bonding a specific number of organic ring groups. The method for producing a carbon nanoring of the present invention comprises a modification step wherein a halogen atom in a U-shaped compound is modified into a boron compound, and a coupling step wherein the U-shaped compound is subjected to a coupling reaction. The U-shaped compound is a novel compound that has cyclohexane rings, benzene rings, and specific organic ring groups.

8 Claims, No Drawings

CARBON NANORING, METHOD FOR PRODUCING SAME, COMPOUND SUITABLE AS STARTING MATERIAL FOR PRODUCING THE CARBON NANORING, AND METHOD FOR PRODUCING THE COMPOUND

TECHNICAL FIELD

The present invention relates to a carbon nanoring as a new compound in which organic ring groups such as bivalent aromatic groups are circularly bonded, and a method for producing such a carbon nanoring. The present invention also relates to a compound suitable as a raw material of the carbon nanoring, and a method for producing the compound.

BACKGROUND ART

Hitherto-known nano structures containing carbon atoms include single-walled carbon nanotubes made of a cylindrically-rolled two-dimensional graphene sheet, and multi-walled carbon nanotubes containing such carbon nanotubes.

Carbon nanotubes have extremely high mechanical strength and high temperature resistance, and efficiently discharge electrons under voltage application. With these advantageous properties, carbon nanotubes are expected to be applied to various fields, including chemistry, electronics, and life science.

Known methods of manufacturing carbon nanotubes include arc discharge, laser furnaces, chemical vapor deposition, and the like. However, these methods have a disadvantage in that they can only produce mixtures of carbon nanotubes with various diameters and lengths.

As a replacement for tubular nano structures such as carbon nanotubes having a certain length derived from a continuous linkage of carbon atoms, recent studies have focused attention on cyclic nano structures. For example, Non-Patent Document 1 discloses a cycloparaphenylene compound obtained by using cyclohexanedione and diiodobenzene. This compound has a regularly arranged structure having 12 continuously bonded bivalent aromatic groups.

CITATION LIST

Non-Patent Literature

Non-patent literature 1
Takaba, H.; Omachi, H.; Yamamoto, Y.; Bouffard, J.; Itami, K. Angew. Chem. Int. Ed. 2009, 48, 6112

SUMMARY OF INVENTION

Technical Problem

The aforementioned Non-Patent Document 1 discloses only a cycloparaphenylene compound having a regularly arranged structure in which 12 bivalent aromatic groups are continuously bonded. Heretofore, there have been difficulties in developing efficient production of cycloparaphenylene compounds with a larger number of aromatic groups using the disclosed raw materials.

Under such circumstances, an object of the present invention is to provide carbon nanorings of, for example, cycloparaphenylene compounds in which a large number (in particular, 14 or more) of organic ring groups such as bivalent aromatic groups are circularly bonded; methods for producing such carbon nanorings; compounds suitable as the raw material of the carbon nanorings; and methods for producing the compounds.

Solution to Problem

In light of the above object, the inventors of the present invention conducted intensive research, and found that a carbon nanoring in which a large number of organic ring groups are circularly linked can be obtained by the following scheme represented by Reaction Formula 1.

Reaction Formula 1

[Chem. 1]

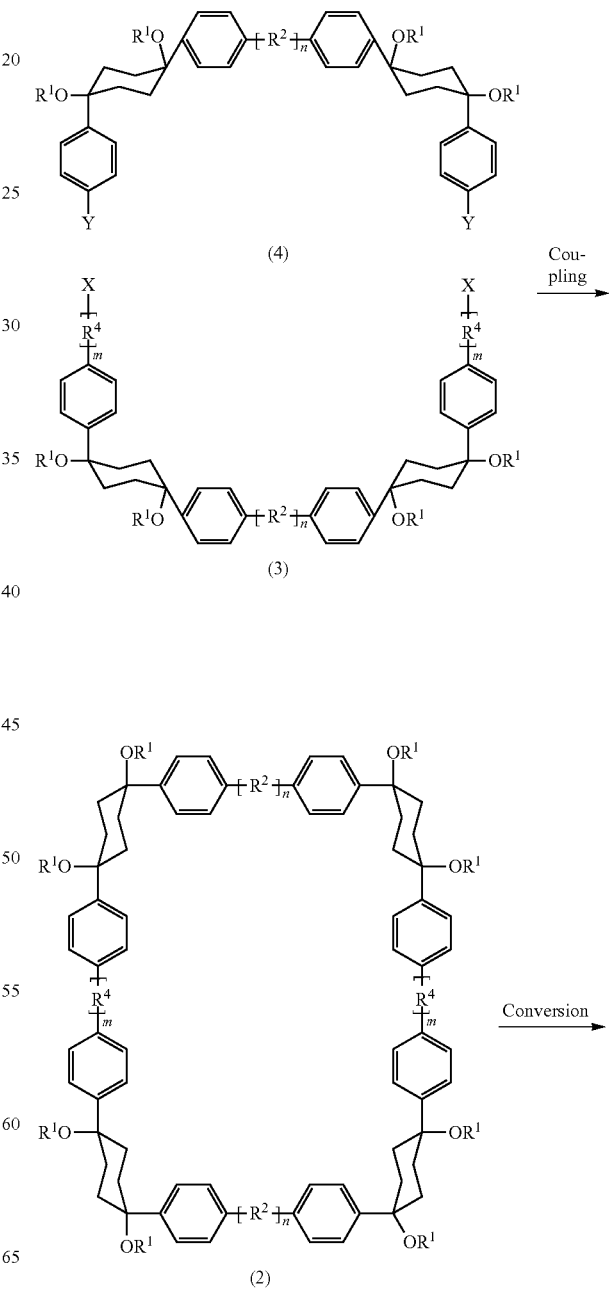

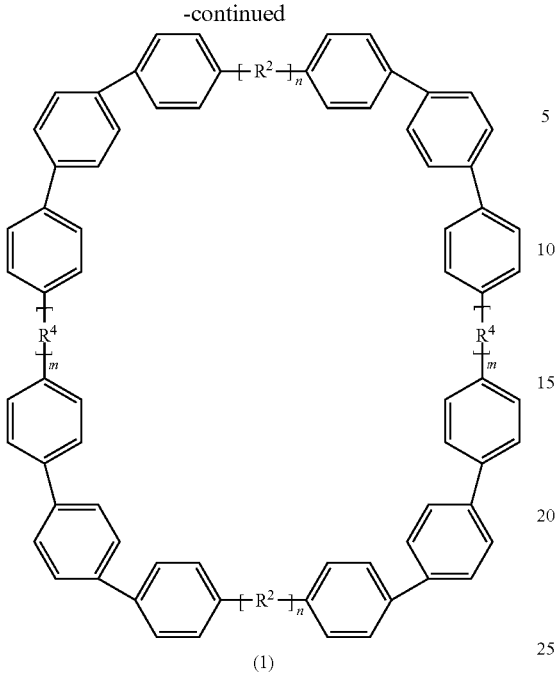

(1)

wherein X is the same or different, and each represents a halogen atom; Y is the same or different, and each represents a group represented by General Formula (9):

[Chem. 2]

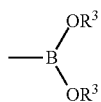
(9)

wherein $R^3$ is the same or different, and each represents a hydrogen atom or $C_1$-$C_{10}$ alkyl group; $R^3$ may be bonded to form a ring with adjacent —O—B—O—);

$R^1$ is the same or different, and each represents a hydrogen atom or a protecting group for a hydroxy group; $R^2$ is the same or different, and each represents a bivalent aromatic hydrocarbon group, a bivalent alicyclic hydrocarbon group, a bivalent heterocyclic group, or a derivative group thereof; $R^4$ is the same or different, and each represents a bivalent aromatic hydrocarbon group, a bivalent alicyclic hydrocarbon group, a bivalent heterocyclic group, or a derivative group thereof; n is the same or different, and each represents an integer of 1 or more; m is the same or different, and each represents an integer of 0 or more.

The present invention was completed as a result of further research based on the above findings. More specifically, the present invention includes carbon nanorings, methods for producing the carbon nanorings, compounds suitable as the raw materials of the carbon nanorings, and methods for producing the compounds. These products and methods include the following Items 1 to 14.

Item 1. A cyclic compound represented by General Formula (2):

[Chem. 3]

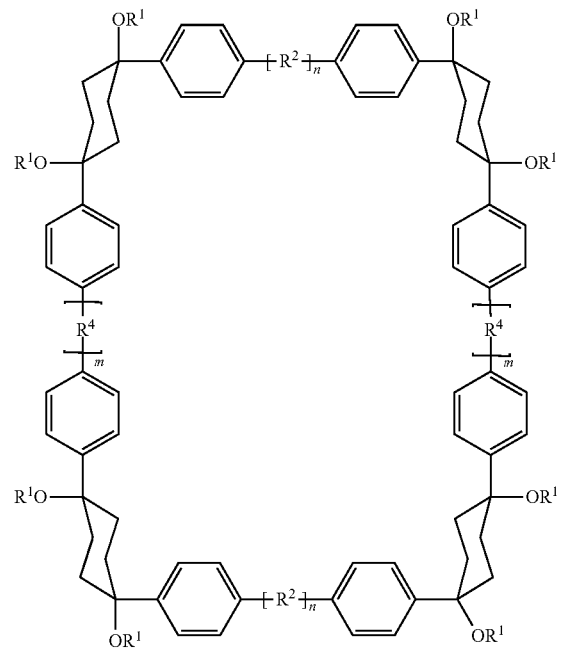
(2)

wherein $R^1$ is the same or different, and each represents a hydrogen atom or a protecting group for a hydroxy group; $R^2$ is the same or different, and each represents a bivalent aromatic hydrocarbon group, a bivalent alicyclic hydrocarbon group, a bivalent heterocyclic group, or a derivative group thereof; $R^4$ is the same or different, and each represents a bivalent aromatic hydrocarbon group, a bivalent alicyclic hydrocarbon group, a bivalent heterocyclic group, or a derivative group thereof; n is the same or different, and each represents an integer of 1 or more; and m is the same or different, and each represents an integer of 0 or more.

Item 2. A method for producing a carbon nanoring represented by General Formula (1):

(1)

[Chem. 4]

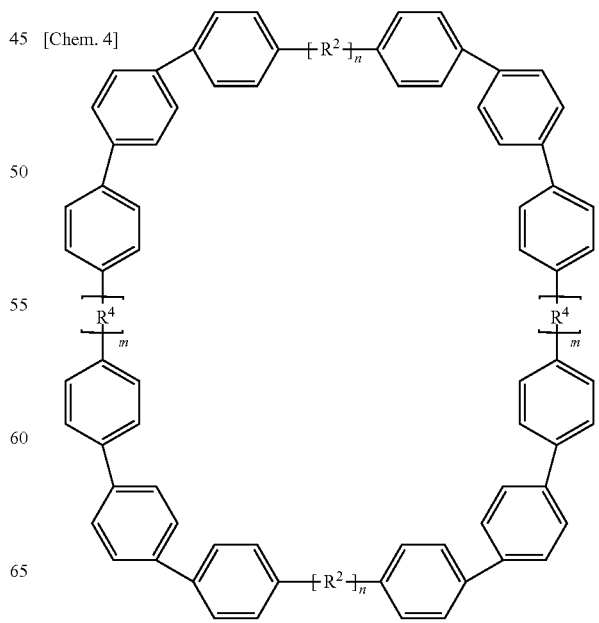

wherein $R^2$ is the same or different, and each represents a bivalent aromatic hydrocarbon group, a bivalent alicyclic hydrocarbon group, a bivalent heterocyclic group, or a derivative group thereof; $R^4$ is the same or different, and each represents a bivalent aromatic hydrocarbon group, a bivalent alicyclic hydrocarbon group, a bivalent heterocyclic group, or a derivative group thereof; n is the same or different, and each represents an integer of 1 or more; and m is the same or different, and each represents an integer of 0 or more, the method comprising a conversion step of: converting cyclohexane rings of a cyclic compound represented by General Formula (2):

[Chem. 5]

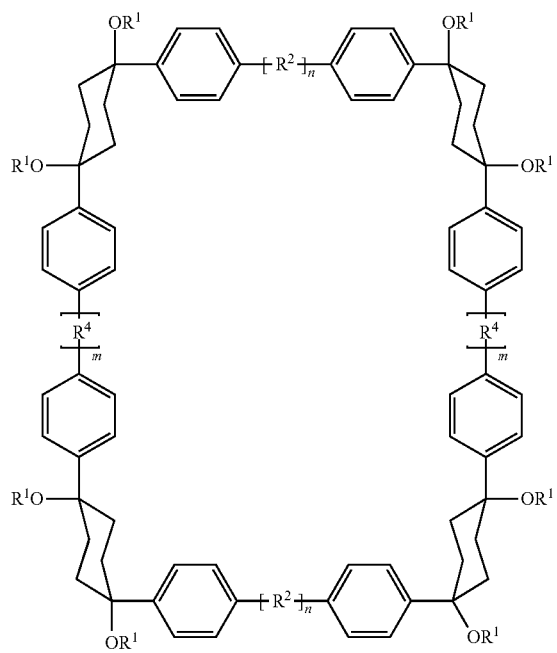

(2)

wherein $R^1$ is the same or different, and each represents a hydrogen atom or a hydroxyl protecting group; and $R^2$, $R^4$, n and m are as defined above, into benzene rings.

Item 3. A method for producing the carbon nanoring according to Item 2 represented by General Formula (1), the method comprising, before the conversion step, a coupling step of:

performing a coupling reaction of a compound represented by General Formula (3):

[Chem. 6]

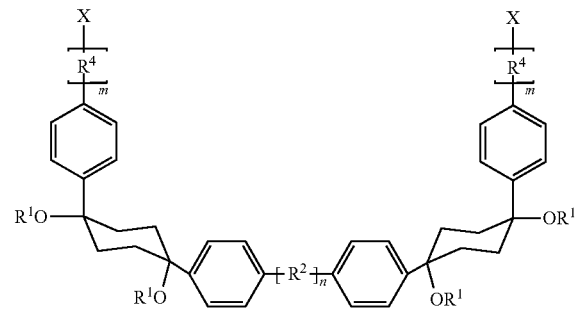

(3)

wherein X is the same or different, and each represents a halogen atom; and $R^1$, $R^2$, $R^4$, n and m are as defined above, and a compound represented by General Formula (4):

[Chem. 7]

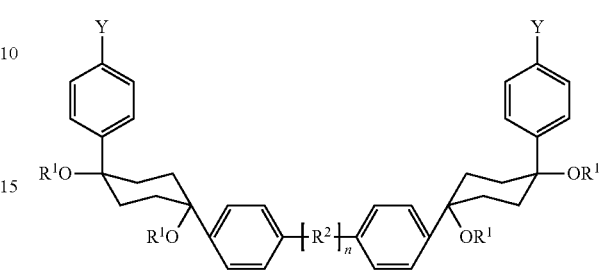

(4)

wherein Y is the same or different, and each represents a group represented by General Formula (9):

[Chem. 8]

(9)

wherein $R^3$ is the same or different, and each represents a hydrogen atom or a $C_1$-$C_{10}$ alkyl group; and $R^3$ may be bonded to form a ring with adjacent —O—B—O—;

and $R^1$, $R^2$ and n are as defined above, to form the cyclic compound represented by General Formula (2).

Item 4. A carbon nanoring represented by General Formula (1):

(1)

[Chem. 9]

wherein $R^2$ is the same or different, and each represents a bivalent aromatic hydrocarbon group, a bivalent alicyclic hydrocarbon group, a bivalent heterocyclic group, or a derivative group thereof; $R^4$ is the same or different, and each represents a bivalent aromatic hydrocarbon group, a bivalent alicyclic hydrocarbon group, a bivalent heterocyclic group, or a derivative group thereof; n is the same or different, and each represents an integer of 1 or more; and m is the same or different, and each represents an integer of 0 or more.

Item 5. The carbon nanoring according to Item 4, wherein $R^2$ and $R^4$ are the same or different, and each represents a group containing a bivalent 6-membered aromatic ring or a bivalent 6-membered heterocyclic aromatic ring, and is bonded at the para-positions.

Item 6. The carbon nanoring according to Item 4, wherein —$(R^2)_n$— is the same or different, and is represented by General Formula (5):

[Chem. 10]

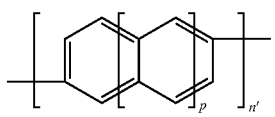

(5)

wherein n' is 1 or 2; and p is 0, 1, 2 or 3.

Item 7. The carbon nanoring according to any one of Items 4 to 6, wherein —$(R^4)_m$— is the same or different, and is represented by General Formula (7):

[Chem. 11]

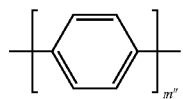

(7)

wherein m" is 1, 2, or 3,
or General Formula (8):

[Chem. 12]

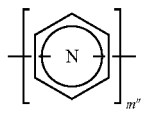

(8)

wherein m" is 1, 2 or 3; and a ring of a repeating unit is a 6-membered heterocyclic aromatic ring having nitrogen.

Item 8. The carbon nanoring according to any one of Items 4 to 7, wherein the total number of phenylenes, $R^2$, and $R^4$ in the carbon nanoring is 13, 14, 15, 16, 17, 19 or 20.

Item 9. The carbon nanoring according to any one of Items 4 to 8, wherein $R^2$ and $R^4$ are all phenylenes, and the total number of phenylenes is 13, 14, 15, 16, 17, 19 or 20.

Item 10. The carbon nanoring according to any one of Items 4 to 7, wherein n is 1 or 2.

Item 11. The carbon nanoring according to any one of Items 4 to 7, wherein m is an integer of 0 to 3.

Item 12. A method for producing a cyclic compound represented by General Formula (2):

[Chem. 13]

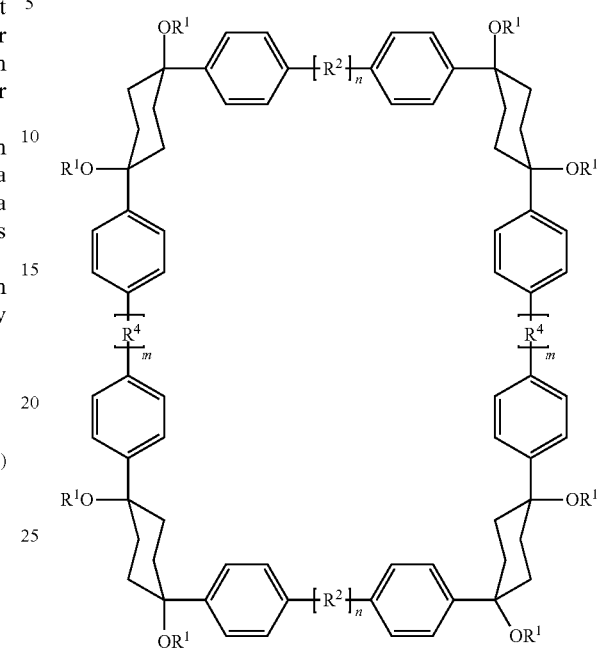

(2)

wherein $R^1$ is the same or different, and each represents a hydrogen atom or a protecting group for a hydroxy group; $R^2$ is the same or different, and each represents a bivalent aromatic hydrocarbon group, a bivalent alicyclic hydrocarbon group, a bivalent heterocyclic group, or a derivative group thereof; $R^4$ is the same or different, and each represents a bivalent aromatic hydrocarbon group, a bivalent alicyclic hydrocarbon group, a bivalent heterocyclic group, or a derivative group thereof; n is the same or different, and each represents an integer of 1 or more; and m is the same or different, and each represents an integer of 0 or more.

the method comprising a coupling step of performing a coupling reaction of a compound represented by General Formula (3):

[Chem. 14]

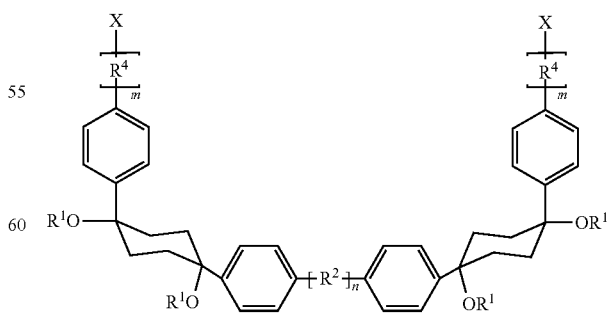

(3)

wherein X is the same or different, and each represents a halogen atom; and $R^1$, $R^2$, $R^4$, n and m are as defined above, and a compound represented by General Formula (4):

[Chem. 15]

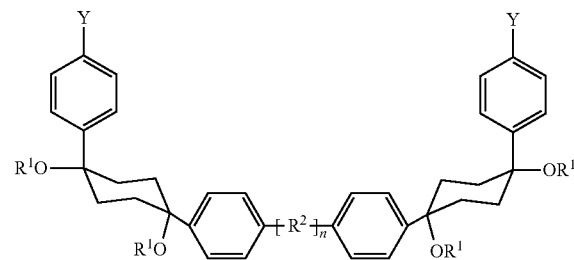
(4)

wherein Y is the same or different, and each represents a group represented by General Formula (9):

[Chem. 16]

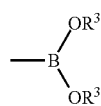
(9)

wherein $R^3$ is the same or different, and each represents a hydrogen atom or a $C_1$-$C_{10}$ alkyl group; $R^3$ may be bonded to form a ring with adjacent —O—B—O—, and $R^1$, $R^2$ and n are as defined above, to form the cyclic compound represented by General Formula (2).

Item 13. A compound represented by General Formula (3):

[Chem. 17]

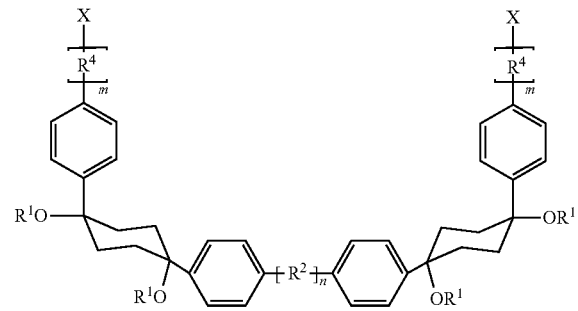
(3)

wherein X is the same or different, and each represents a halogen atom; $R^1$ is the same or different, and each represents a hydrogen atom or a protecting group for a hydroxy group; $R^2$ each represents a bivalent aromatic hydrocarbon group, a bivalent alicyclic hydrocarbon group, a bivalent heterocyclic group, or a derivative group thereof; $R^4$ is the same or different, and each represents a bivalent aromatic hydrocarbon group, a bivalent alicyclic hydrocarbon group, a bivalent heterocyclic group, or a derivative group thereof; n is an integer of 1 or more; and m is the same or different, and each represents an integer of 0 or more.

Item 14. A method for producing a compound represented by General Formula (3):

[Chem. 18]

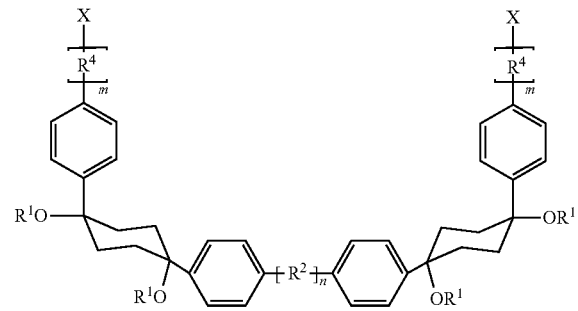
(3)

wherein X is the same or different, and each represents a halogen atom; $R^1$ is the same or different, and each represents a hydrogen atom or a protecting group for a hydroxy group; $R^2$ each represents a bivalent aromatic hydrocarbon group, a bivalent alicyclic hydrocarbon group, a bivalent heterocyclic group, or a derivative group thereof; $R^4$ is the same or different, and each represents a bivalent aromatic hydrocarbon group, a bivalent alicyclic hydrocarbon group, a bivalent heterocyclic group, or a derivative group thereof; n is an integer of 1 or more; and m is the same or different, and each represents an integer of 0 or more, the method comprising a reaction step of reacting, in the presence of a palladium catalyst, raw materials containing Compound (10) represented by General Formula (10):

[Chem. 19]

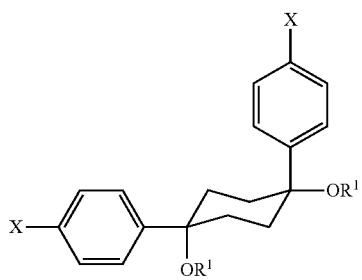
(10)

wherein X and $R^1$ are as defined above, and Compound (11) represented by General Formula (11):

[Chem. 20]

(11)

wherein $R^2$ and n are as defined above; Y is the same or different, and each represents a group represented by General Formula (9):

[Chem. 21]

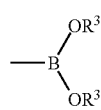
(9)

wherein $R^3$ is the same or different, and each represents a hydrogen atom or a $C_1$-$C_{10}$ alkyl group; and $R^3$ may be bonded to form a ring with adjacent —O—B—O—.

Effects of Invention

The carbon nanoring of the present invention is a compound having a cyclic structure with a large number of organic ring groups. Such a carbon nanoring is suitable as a electronic industry material, luminescence material, and the like.

Further, when a carbon nanoring of the present invention is a cycloparaphenylene compound having 13 or more phenylene groups (in particular, 1,4-phenylene groups), the carbon nanoring is useful as a raw material for the synthesis of carbon nanotubes having a diameter corresponding to the number of phenylene groups. The resulting carbon nanorings are suitable as, in particular, electronic industry materials, luminescence materials, and the like.

The method for producing carbon nanorings of the present invention enables efficient production of carbon nanorings made of symmetrical or asymmetrical cyclic compounds in which at least 13 organic ring groups are continuously bonded. Further, by using U-shaped compounds (3) and (4) having two cyclohexane rings at each corner, it is possible to produce carbon nanorings having a desired number of organic ring groups.

Compound (3) used as a raw material of the present invention contains, at each molecular terminus, an organic ring group such as a benzene ring having a halogen atom, a cyclohexane ring attached to the organic ring group, and the like. Each cyclohexane ring is attached to the benzene rings at the 1-position and 4-position, forming a nonlinear (L-shaped) structure of chair conformation in which the benzene rings are respectively at axial and equatorial positions. Accordingly, the compound represented by General Formula (3) generally has an overall U-shape. By subjecting the compound represented by General Formula (3) and the compound represented by General Formula (4) to a coupling reaction, a cyclic compound represented by General Formula (2) is formed. Compound (4) represented by General Formula (4) can be easily synthesized using the compound represented by General Formula (3). Further, by modifying the structures of the compound represented by General Formula (3) and the compound represented by General Formula (4) used as raw materials, it is possible to efficiently produce, for example, carbon nanorings having a cyclic structure in which an arbitrary number of organic ring groups are continuously bonded.

DESCRIPTION OF EMBODIMENTS

[1] Carbon Nanoring

The carbon nanoring of the present invention is represented by General Formula (1):

[Chem. 22]

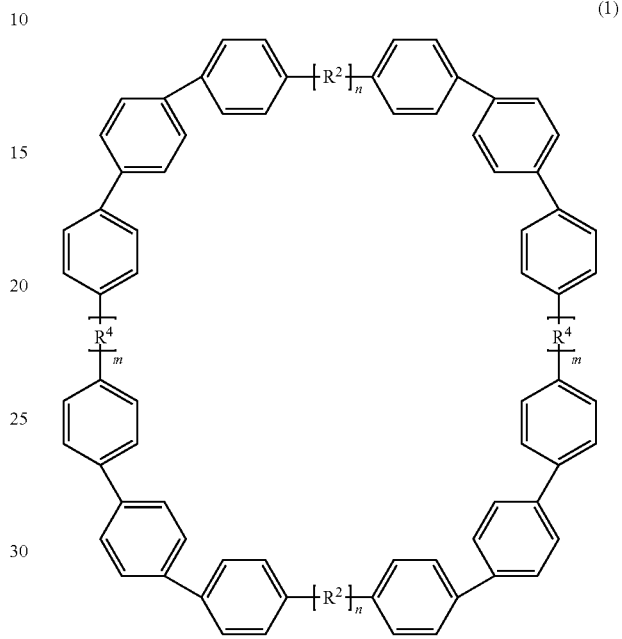
(1)

wherein $R^2$ is the same or different, and each represents a bivalent aromatic hydrocarbon group, a bivalent alicyclic hydrocarbon group, a bivalent heterocyclic group, or a derivative group thereof; $R^4$ is the same or different, and each represents a bivalent aromatic hydrocarbon group, a bivalent alicyclic hydrocarbon group, a bivalent heterocyclic group, or a derivative group thereof; n is the same or different, and each represents an integer of 1 or more; and m is the same or different, and each represents an integer of 0 or more.

In General Formula (1), $R^2$ represents a bivalent aromatic hydrocarbon group, a bivalent alicyclic hydrocarbon group, a bivalent heterocyclic group, or a derivative group thereof (hereinafter, they may be collectively referred to as "bivalent organic ring groups"). In other words, the bivalent organic ring group $R^2$ is a bivalent group containing an organic ring selected from aromatic rings, cycloalkanes and heterocyclic rings, obtained by detaching a hydrogen atom from each of the two carbon atoms of the organic ring. The hydrogen atom bonded to each of the two carbon atoms of the organic ring may be a derivative group (bivalent derivative group) substituted with a functional group. $R^2$ may be the same or different.

In addition to benzene rings, examples of the aromatic rings also include rings resulting from the condensation of multiple benzene rings (benzene condensed rings) and rings resulting from the condensation of benzene and other rings (hereinafter, these rings resulting from the condensation of multiple benzene rings and rings resulting from the condensation of benzene and other rings may be collectively referred to as "condensed rings"). Examples of the condensed rings include a pentalene ring, indene ring, naphthalene ring, anthracene ring, tetracene ring, pentacene ring, pyrene ring, perylene ring, triphenylene ring, azulene ring, heptalene ring, biphenylene ring, indacene ring, acenaphthylene ring, fluorene ring, phenalene ring, and phenanthrene ring.

The cycloalkanes are not limited insofar as they have 3 to 10 carbon atoms, such as cyclopropane, cyclohexane, or the like.

Examples of the heterocyclic rings include heterocyclic rings (namely, heterocyclic aromatic rings and heterocyclic aliphatic rings, in particular, heterocyclic aromatic rings) having at least one atom selected from a nitrogen atom, oxygen atom, boron atom, phosphorus atom, silicon atom and sulfur atom. Examples of heterocyclic rings include a furan ring, thiophene ring, pyrrole ring, silole ring, borole ring, phosphole ring, oxazole ring, thiazole ring, pyridine ring, pyridazine ring, pyrimidine ring, and pyrazine ring. Heterocyclic condensed rings obtained by combining these rings, these rings and benzene rings, or these rings and the aforementioned condensed rings, may also be used. The examples of the heterocyclic condensed rings are thienothiophene rings, quinoline rings, and the like.

Among these rings, $R^2$ is preferably a group that contains a bivalent 6-membered aromatic ring or a bivalent 6-membered heterocyclic aromatic ring, and is bonded at the para-positions.

Further, the organic ring of $R^2$ is preferably a monocyclic or condensed ring. A monocyclic ring is more preferable.

Among these, $R^2$ in General Formula (1) above is preferably a bivalent aromatic hydrocarbon group, in particular, a phenylene group (in particular, a 1,4-phenylene group) and a naphthylene group (in particular, a 1,5-naphthylene group or 2,6-naphthylene group). A phenylene group (in particular, a 1,4-phenylene group) is more preferable.

As with $R^2$, $R^4$ also represents a bivalent organic ring group containing an organic ring selected from aromatic rings, cycloalkanes and heterocyclic rings, obtained by detaching a hydrogen atom from each of the two carbon atoms of the organic ring. $R^4$ may be the same or different. However, the synthesis is easy if they are the same. $R^4$ may be the same as $R^2$, or different from $R^2$.

In addition to benzene rings, examples of the aromatic rings also include rings resulting from the condensation of multiple benzene rings (benzene condensed rings) and rings resulting from the condensation of benzene and other rings. Examples of the condensed rings include a pentalene ring, indene ring, naphthalene ring, azulene ring, heptalene ring, biphenylene ring, indacene ring, acenaphthylene ring, fluorene ring, phenalene ring, phenanthrene ring, and anthracene ring.

The cycloalkanes are not limited insofar as they have 3 to 10 carbon atoms, such as cyclopropane, cyclohexane or the like.

Examples of the heterocyclic rings include heterocyclic rings (namely, heterocyclic aromatic rings or heterocyclic aliphatic rings, in particular, heterocyclic aromatic rings) having at least one atom selected from a nitrogen atom, oxygen atom, boron atom, phosphorus atom, silicon atom and sulfur atom. Examples of heterocyclic rings include a furan ring, thiophene ring, pyrrole ring, oxazole ring, thiazole ring, pyridine ring, pyridazine ring, pyrimidine ring, and pyrazine ring. Heterocyclic condensed rings obtained by combining these rings, these rings and benzene rings, or these rings and the aforementioned condensed rings may also be used. The examples of the heterocyclic condensed rings are thienothiophene rings, quinoline rings, and the like.

Among these rings, $R^4$ is preferably a group that contains a bivalent 6-membered aromatic ring or a bivalent 6-membered heterocyclic aromatic ring, and is bonded at the para-positions.

Further, the organic ring of $R^4$ is preferably a monocyclic or condensed ring. A monocyclic ring is more preferable.

Among these, $R^4$ in General Formula (1) above is preferably a phenylene group (in particular, a 1,4-phenylene group), a pyridylidene group (in particular, a 2,5-pyridylidene group) or a pyrimidinylidene group (in particular, a 2,5-pyrimidinylidene group).

By introducing an organic ring group as $R^4$, it is possible to form a carbon nanoring having a cyclic structure with a larger number of organic ring groups, compared with a case without such introduction. As such, the structure of the ring can be arbitrarily adjusted depending on the structures of $R^2$ and $R^4$.

Further, $R^2$ and $R^4$ may contain hetero atoms. Thereby, various carbon nanorings can be formed.

Further, by using groups having a condensed ring, such as a naphthalene ring or anthracene ring, as $R^2$ and $R^4$, it is possible to form a chiral carbon nanoring. More specifically, by using groups having a condensed ring as $R^2$ and $R^4$ in the later-described production method of the present invention, it is possible to efficiently obtain a chiral carbon nanoring (carbon nanotube) containing a specific number of organic rings.

In General Formula (1), n is an integer of 1 or more, preferably not more than 10, more preferably not more than 5, further preferably not more than 3, and particularly preferably 1 or 2. When n is 2 or more, the compound has a structure in which multiple $R^2$ are directly bonded. In this direct bond, $R^2$ may be the same or different.

In General Formula (1), "—$(R^2)_n$—" is preferably a group represented by General Formula (5):

[Chem. 23]

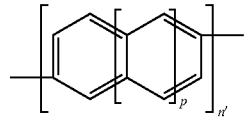

(5)

wherein n' is 1 or 2; and p is 0, 1, 2 or 3.

It is particularly preferable that the group represented by General Formula (5) be a phenylene group in which n' is 1 and p is 0 (namely, a 1,4-phenylene group), a biphenylene group in which n' is 2 and p is 0 (namely, a 4,4'-biphenylene group), or a naphthylene group in which n' is 1 and p is 1 (namely, a 2,6-naphthylene group), as in Formula (6) below.

[Chem. 24]

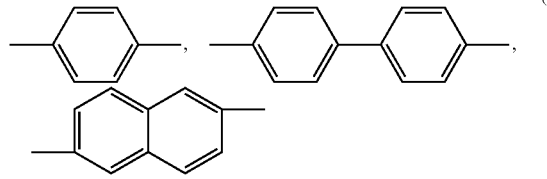

(6)

In General Formula (1), m is an integer of 0 or more, preferably not more than 10, more preferably not more than 5, further preferably not more than 3, and particularly preferably 1 or 2. When m is 2 or more, the compound has a structure in which multiple R⁴ are directly bonded. In this direct bond, R⁴ may be the same or different.

In General Formula (1), "—(R⁴)$_m$—" is preferably a group represented by General Formula (7):

[Chem. 25]

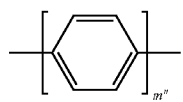
(7)

wherein m" is 1, 2, or 3,
or General Formula (8):

[Chem. 26]

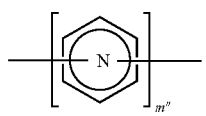
(8)

wherein m" is 1, 2, or 3.

The ring of the repeating unit in General Formula (8) represents a 6-membered heterocyclic aromatic ring. Further, when m" is 2 or more, the rings may be the same or different. When m" in General Formula (8) is 2 or more, the rings may be bonded at the same or different positions. Preferably, all rings are bonded at the para-positions.

Particularly preferably, "—(R⁴)$_m$—" is a group represented by General Formula (7a):

[Chem. 27]

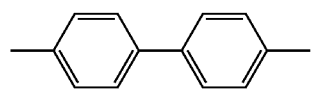
(7a)

or General Formula (8a):

[Chem. 28]

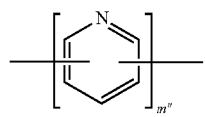
(8a)

wherein m" is as defined above,
and more preferably, a group represented by General Formula (7a) or General Formula (8b).

[Chem. 29]

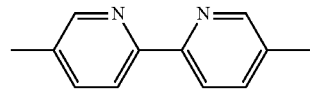
(8b)

The carbon nanoring of the present invention has 13 or more bivalent organic ring groups. Although the number of organic ring groups is not particularly limited, it is typically not more than 100, preferably not more than 50, more preferably not more than 30, further preferably not more than 20, more preferably not more than 18, further preferably 13 to 17, particularly preferably 13 to 16, further preferably 14 to 16. The later-described production method of the present invention is capable of producing carbon nanorings in which the total number of the organic ring groups (i.e., phenylene groups, R², R⁴) is 13, 14, 15, 16, 17, 18, 19, or 20. More specifically, the method of the present invention is capable of producing carbon nanorings in which the total number of organic ring groups is not only a multiple of 3 (e.g., 15, 18, etc.), but also multiples of other numbers (that is, the method is capable of producing carbon nanorings in which the total number of organic ring groups is 13, 14, 16, 17, 19, or 20).

Further, the diameter of the carbon nanorings of the present invention is about 1.8 to 2.4 nm when the nanoring has 13 to 16 organic ring groups (in particular, a phenylene group). Further, the diameter is about 1.8 to 2.5 nm when the nanoring has 13 to 18 organic ring groups (in particular, a phenylene group).

Further, in the carbon nanorings of the present invention, it is preferable that at least 8 organic ring groups are derived from aromatic rings. It is preferable that all of the organic ring groups be aromatic hydrocarbon groups. It is further preferable that the carbon nanorings be made of compounds in which all of the organic ring groups are phenylene groups.

Further, in the carbon nanorings of the present invention, if all of the organic ring groups in the compound of the nanoring are phenylene groups, it is particularly preferable that the compound be a cycloparaphenylene compound having 13 to 18, and in particular, 13 to 16 phenylene groups. In this cycloparaphenylene compound, the phenylene groups are preferably directly bonded at the 1 positions and 4-positions.

Further, among such cycloparaphenylene compounds, General Formula (1a) below represents a cycloparaphenylene compound having 14 to 18 benzene rings:

[Chem. 30]

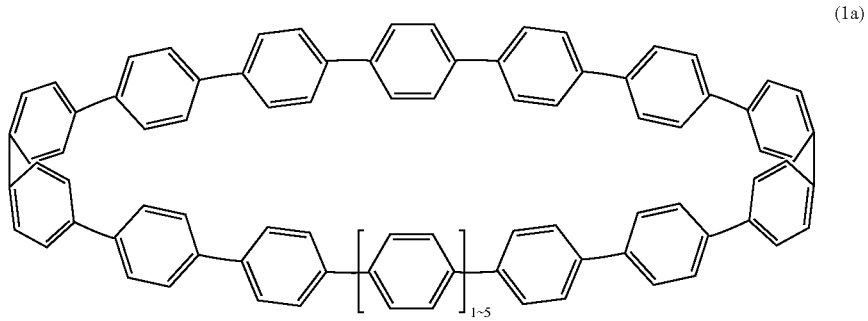

(1a)

The cycloparaphenylene compound containing a specific number of benzene rings, such as 13 to 18, and in particular, 13 to 16 benzene rings, as in General Formula (1a) is useful as a raw material for synthesizing (pure synthesis) a carbon nanotube having a uniform radius. Such a cycloparaphenylene compound is also suitable for electronic industry materials, luminescence materials, and the like.

[2] Production Method for Carbon Nanorings

The carbon nanoring of the present invention can be produced through the following scheme represented by Reaction Formula 1:

Reaction Formula 1

[Chem. 31]

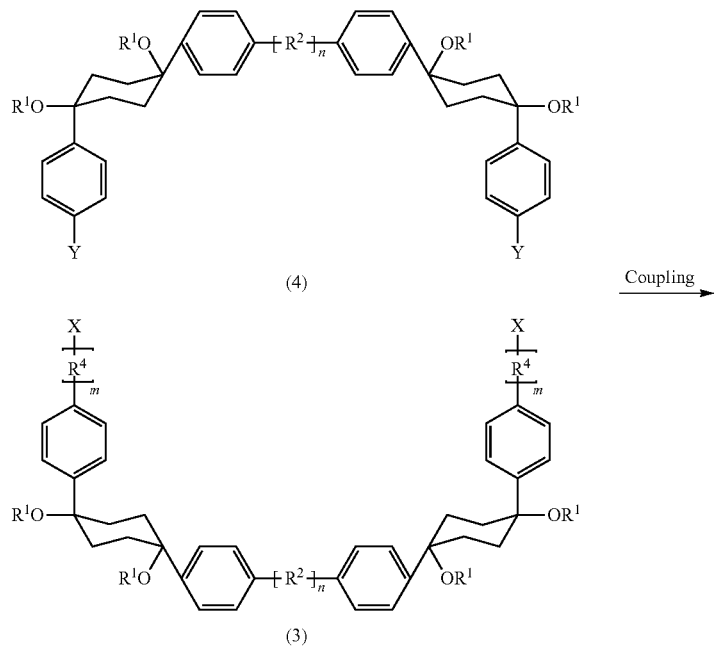

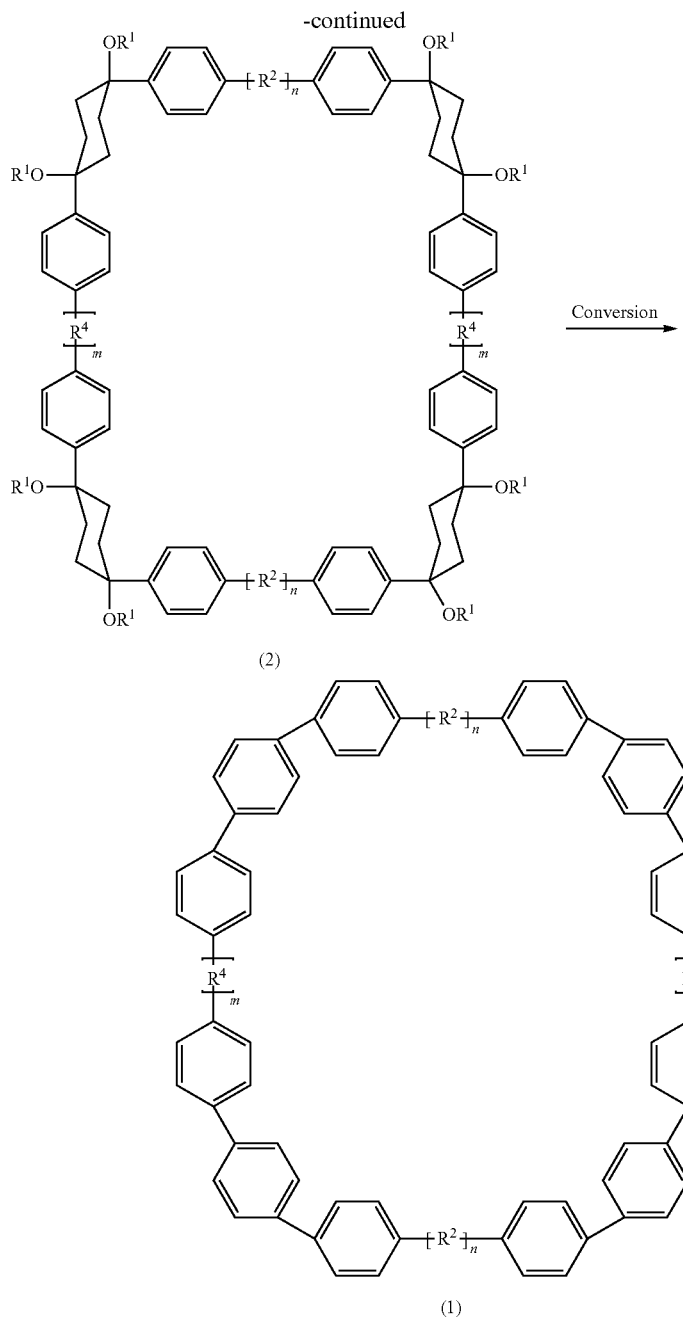

(2)

(1)

wherein X is the same or different, and each represents a halogen atom; Y is the same or different, and each represents a group represented by General Formula (9):

[Chem. 32]

(9)

wherein $R^3$ is the same or different, and each represents a hydrogen atom or a $C_1$-$C_{10}$ alkyl group; $R^3$ may be bonded to form a ring with adjacent —O—B—O—);

$R^1$ is the same or different, and each represents a hydrogen atom or a protecting group for a hydroxy group; and $R^2$, $R^4$, n and m are the same as those in General Formula (1).

In General Formula (3) of Reaction Formula 1, X is not particularly limited insofar as it is a halogen atom. Examples thereof include a fluorine atom, chlorine atom, bromine atom, and iodine atom. In the present invention, a bromine atom and an iodine, atom are preferable, and a bromine atom is particularly preferable. Further, in General Formula (3), the two Xs are the same or different.

Further, in General Formula (3) of Reaction Formula 1, Y is a monovalent group represented by General Formula (9) (hereinafter, the monovalent group may also be referred to as "boronic acid (or esters thereof) group"). In General Formula (3), the two Ys are the same or different.

The boronic acid (or esters thereof) group represented by $R^3$ in General Formula (9) is a hydrogen atom or an alkyl group. The alkyl group has 1 to 10, preferably 1 to 8, and more preferably 1 to 5 carbon atoms. Further, the two $R^3$ may be the same or different. When $R^3$ is an alkyl group, the carbon atoms of the alkyl group may be bonded to form a ring with the boron atoms and the oxygen atoms.

In General Formula (9), for example, Y may be a group represented by Formulae (9a) to (9c) below:

[Chem. 33]

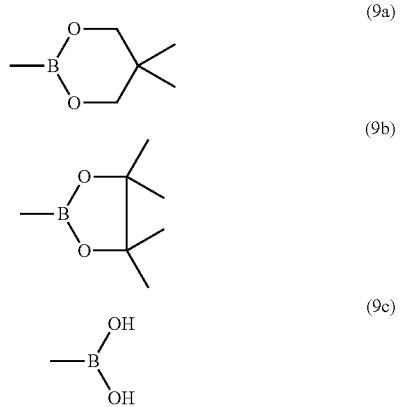

When Y in General Formula (3) is a group represented by Formulae (9a) to (9c), it is possible to more efficiently perform the reaction between the compound represented by General Formula (3) and the compound represented by General Formula (4).

The steps in the reaction are described below.

1. Conversion Step of Converting Cyclic Compound (2) into a Carbon Nanoring (1)

The carbon nanoring of the present invention represented by General Formula (1) (which may also be referred to as "Carbon Nanoring (1)" hereinafter) can be obtained through a conversion step of converting the cyclohexane rings of the cyclic compound represented by General Formula (2) (which may also be referred to as "Cyclic Compound (2)" hereinafter) of the present invention in Reaction Formula 1 into benzene rings.

For example, this step may be performed by a general oxidation reaction. For example, a method of heating Cyclic Compound (2) in the presence of acid (acid-treatment), a method of heating the compound in the presence of oxygen (in air atmosphere, oxygen atmosphere, etc.), a reaction with quinones, metallic oxidants, etc., may be adopted. Such processes are generally performed by a dehydrogenation reaction or the like, thereby chemically changing (aromatizing) the cyclohexane rings of Cyclic Compound (2) into benzene rings to synthesize Carbon Nanoring (1). More specifically, the above processes eliminate the $OR^1$ that exists in each cyclohexane ring of the cyclic compound before conversion, while performing the dehydrogenation reaction, thereby yielding Carbon Nanoring (1).

Further, in General Formula (2), $R^2$, $R^4$, m and n are as defined above in General Formula (1) for Carbon Nanoring (1) of the present invention.

In General Formula (2), $R^1$ represents a hydrogen atom or a protecting group for a hydroxy group. The hydroxyl protecting group is not particularly limited. Examples thereof include a methoxymethyl group ($—CH_2—O—CH_3$, which may be referred to as "-MOM" hereinafter), alkanoyl group (e.g., an acetyl group, propionyl group, etc.), a silyl group (e.g., a trimethylsilyl group, triethylsilyl group, t-butyldimethylsilyl group, etc.), a tetrahydropyranyl group (THP), an alkyl group (e.g., methyl group, ethyl group, etc.), and a benzyl group. A methoxymethyl group is preferable.

The protecting group (in particular, a methoxymethyl group) is substituted with a hydrogen atom of alcohol (hydroxyl group), thereby serving as a protecting group of the alcohol.

Further, among the protecting groups, methoxymethyl group is obtained by reacting the alcohol to be protected with chloromethylmethylether ($Cl—CH_2—O—CH_3$).

Further, in General Formula (2), the eight $R^1$ groups are the same or different. When the later-described Compound (3) is used as a raw material of Carbon Nanoring (1), $R^1$ is preferably a methoxymethyl group ($—CH_2—O—CH_3$).

The method of the above acid treatment is not particularly limited. Preferable examples thereof include the following methods.

(A) A method of dissolving Cyclic Compound (2) and an acid in a solvent, and reacting the resulting solution by heating.

(B) A method of dissolving Cyclic Compound (2) in a solvent, mixing the resulting solution with an acid, and reacting the resulting mixture by heating.

In the above conversion step, the acid treatment can be performed without a solvent.

Other examples of acid treatment include the following.

The acid is not particularly limited; however, strong acids used for catalysts or the like are preferable. Examples thereof include sulfuric acids, methanesulfonic acids, para-toluenesulfonic acids, tungstophosphoric acids, tungstosilicic acids, molybdophosphoric acids, molybdosilicic acids, boron trifluoride etherates, and tin tetrachlorides. They may be used singly or in a combination of two or more.

The acid amount may be varied depending on the production conditions, etc. In Method (A) above, the acid amount is preferably 0.01 to 100 molar equivalents, more preferably 0.5 to 50 molar equivalents, and yet more preferably 1 to 20 molar equivalents, relative to Cyclic Compound (2).

In Method (B) above, the acid amount is preferably 0.01 to 100 molar equivalents, more preferably 0.5 to 50 molar equivalents, and yet more preferably 1 to 20 molar equivalents, relative to Cyclic Compound (2).

Both nonpolar solvents and polar solvents may be used as solvents for the acid treatment reaction. Examples thereof include alkanes such as hexane, heptane, or octane; haloalkanes such as methylene chloride, chloroform, carbon tetrachloride, or ethylene chloride; benzenes such as benzene, toluene, xylene, mesitylene, or pentamethylbenzene; halobenzenes such as chrolobenzene or bromobenzene; ethers such as diethyl ether or anisole; and dimethylsulfoxides. These solvents may be used singly or in a combination of two or more. In the reaction using a solvent, the reaction intermediate between the raw material and Carbon Nanoring (1) may have low solubility with respect to the Solvent used in this Step. In this case, another solvent may be added in advance or during the reaction.

When a solvent is used, the amount thereof is appropriately determined depending on the production conditions. However, it is preferable that the amount of solvent be 100 to 100,000 parts by mass, and more preferably 1,000 to 10,000 parts by mass, based on 100 parts by mass of Cyclic Compound (2).

The heating temperature in Methods (A) and (B) above is generally 50° C. or more, preferably 80° C. or more, more preferably 100° C. or more, and yet more preferably 120° C. or more. When a solvent is used, the temperature is set in a range of not more than the boiling point of the solvent.

The heating is performed by using, for example, an oil bath, an aluminum block constant-temperature bath, a heat gun, a burner, microwave irradiation, etc. In the case of microwave irradiation, it is possible to use a known microwave reaction device for microwave reaction. Reflux cooling may be performed together with the heating process.

The reaction atmosphere in the acid treatment is not particularly limited; an inert gas atmosphere, such as an argon gas atmosphere or a nitrogen gas atmosphere, is preferable. An air atmosphere may also be adopted.

When the above conversion step is performed using Cyclic Compound (2) represented by General Formula (2) in which $—(R^2)_n—$ are all carbon atoms, the resulting Carbon Nanoring (1) contains 14 or more continuous bivalent organic ring groups. Further, when the above conversion step is performed using Cyclic Compound (2) in which $R^2$ is an aromatic hydrocarbon group, such as a phenylene group, a cyclic cycloparaphenylene compound or the like can be obtained.

When the above conversion step is performed using Cyclic Compound (2) represented by General Formula (2) in which both $—(R^2)_n—$ and $—(R^4)_m—$ are all carbon atoms, the resulting Carbon Nanoring (1) contains 16 or more continuous bivalent organic ring groups. Further, when the above conversion step is performed using Cyclic Compound (2) in which $R^4$ is an aromatic hydrocarbon group, such as a phenylene group, a cyclic cycloparaphenylene compound or the like can be obtained.

Furthermore, when the above conversion step is performed using Cyclic Compound (2) represented by General Formula (2) in which $—(R^2)_n—$ are all carbon atoms, and $—(R^2)_n—$ is a heterocyclic group, the resulting Carbon Nanoring (1) contains 16 or more continuous bivalent organic ring groups and a hetero atom in the molecule.

Further, the method for producing the carbon nanoring of the present invention may also include a purification step after the conversion step as necessary. More specifically, general post-treatment steps, such as solvent removal (when a solvent is used), washing, chromatography separation or the like, may be performed. In particular, because Carbon Nanoring (1) resulting from the conversion step is usually amorphous (non-crystalline), the carbon nanoring can be crystallized using a hitherto-known recrystallization method for organic compounds. In the resulting crystal, the organic solvent used for the recrystallization may be incorporated in the ring of the molecule.

The carbon nanoring obtained by the method for producing carbon nanorings of the present invention contains a compound represented by General Formula (1) having a cyclic structure in which organic ring groups, which are at least one member selected from the group consisting of bivalent aromatic hydrocarbon groups, bivalent alicyclic hydrocarbon groups and bivalent heterocyclic groups, are continuously bonded. The method of the present invention enables the production of a carbon nanoring in which 13 or more, in particular, 14 or more organic ring groups are continuously bonded. The number of organic ring groups is not particularly limited; it is generally not more than 100, preferably not more than 50, more preferably not more than 30, yet more preferably not more than 20, even more preferably not more than 18, and most preferably not more than 17. Furthermore, the method of the present invention enables the production of a carbon nanoring in which the total number of organic ring groups (i.e., phenylene groups $R^2$ and $R^4$) is either 13, 14, 15, 16, 17, 18, 19, or 20. More specifically, the method of the present invention is capable of producing carbon nanorings in which the total number of organic ring groups is not only a multiple of 3 (e.g., 15, 18, etc.), but also multiples of other numbers. That is, the method is capable of producing carbon nanorings in which the total number of the organic ring groups (i.e., phenylene groups $R^2$ and $R^4$) is 13, 14, 16, 17, 19, or 20.

As explained later, the production method of the present invention enables the production of carbon nanorings from various raw materials with diverse structures (Compounds (3) and (4)). Therefore, the resulting Carbon Nanoring (1) has a structure such that the hydrogen atoms bonded to the carbon atoms of the organic ring contained in the cyclic compound are substituted with functional groups.

2. Coupling Step for Obtaining Cyclic Compound (2) from Compounds (3) and (4)

Cyclic Compound (2) used for the above conversion step is obtained through a coupling reaction that reacts the compound represented by General Formula (3) (which may also be referred to as Compound (3) hereinafter) in Reaction Formula 1 with the compound represented by General Formula (4) (which may also be referred to as Compound (4) hereinafter) in Reaction Formula 1 to form a cyclic compound.

The details of Compounds (3) and (4) are described later.

The aforementioned coupling reaction is performed by reacting Compound (3) and Compound (4) using the halogen atom in Compound (3) and the boronic acid (or esters thereof) group (represented by General Formula (9)) in Compound (4).

In the present invention, Cyclic Compound (2) may be obtained by a reaction of Compound (3) and Compound (4) both having a U-shaped structure.

The above reaction of Compound (3) and Compound (4) may be performed using a Suzuki-Miyaura coupling reaction. Suzuki-Miyaura coupling reaction is a carbon-carbon bond reaction and causes a coupling reaction of an aryl halide compound and an organic boron compound. Compound (3) is an aryl halide compound having a halogen atom, and Compound (4) is an organic boron compound having a boronic acid (or esters thereof) group.

In the above coupling reaction step, the amounts of Compound (3) and Compound (4) are as follows. The amount of Compound (4) is preferably 0.8 to 3.0 mol, more preferably 1.0 to 2.0 mol, and yet more preferably 1.2 to 1.8 mol, per mol of Compound (3).

In the above coupling step, as explained, the reaction is generally performed in the presence of a catalyst, preferably, a palladium catalyst. Examples of palladium catalysts include palladium metal and various known palladium compounds to be used as a catalyst for synthesizing organic compounds (including polymer compounds), etc. In the present invention, the palladium catalysts (palladium compounds) usable in a Suzuki-Miyaura coupling reaction may be used. Specific examples thereof include $Pd(PPh_3)_4$ (Ph represents a phenyl group), $PdCl_2(PPh_3)_2$ (Ph represents a phenyl group), $Pd(OAc)_2$ (Ac represents an acetyl group), tris(dibenzylideneacetone)dipalladium(0) $(Pd_2(dba)_3)$ tris(dibenzylideneacetone)dipalladium(0)chloroform complex, bis(dibenzylideneacetone)palladium(0), bis(tri-t-butyl)phosphino)palladium(0), and (1,1'-bis(diphenylphosphino)ferrocene)dichloropalladium(II). In the present step, $Pd(PPh_3)_4$, $Pd_2(dba)_3$, etc. are preferable.

When a palladium catalyst is used in the above coupling step, the amount is, in terms of the yield, generally 0.001 to 1 mol, preferably 0.005 to 0.1 mol, and more preferably 0.01 to 0.05 mol, per mol of Compound (3).

Further, in the above coupling step, as required, it is possible to use, as a catalyst, a phosphorus ligand that can be coordinated with the palladium atom that is the center element of the palladium catalyst. Examples of phosphorus ligands include triphenylphosphine, tri-o-tolylphosphine, tri-m-tolylphosphine, tri-p-tolylphosphine, tris(2,6-dimethoxyphenyl)phosphine, tris[2-(diphenylphosphino)ethyl]phosphine, bis(2-methoxyphenyl)phenylphosphine, 2-(di-t-butylphosphino)biphenyl, 2-(dicyclohexylphosphino)biphenyl, 2-(diphenylphosphino)-2'-(N,N-dimethylamino)biphenyl, tri-t-butylphosphine, bis(diphenylphosphino)methane, 1,2-bis(diphenylphosphino)ethane, 1,2-bis(dimethylphosphino)ethane, 1,3-bis(diphenylphosphino)propane, 1,4-bis(diphenylphosphino)butane, 1,5-bis(diphenylphosphino)pentane, 1,6-bis(diphenylphosphino)hexane, 1,2-bis(dimethylphosphino)ethane, 1,1'-bis(diphenylphosphino)ferrocene, bis(2-diphenylphosphinoethyl)phenylphosphine, 2-(dicyclohexylphosphino-2',6'-dimethoxy-1,1'-biphenyl(X-Phos), 2-(dicyclohexylphosphino-2',4',6'-tri-isopropyl-1,1'-biphenyl(X-Phos), and bis(2-diphenylphosphinophenyl)ether(DPEPhos). In the present step, 2-(dicyclohexylphosphino)-2', 4',6'-tri-isopropyl-1,1'-biphenyl(X-Phos), and the like are preferable.

When a phosphorus ligand is used in the above coupling step, the amount is, in terms of the yield, generally 0.01 to 1.0 mol, preferably 0.05 to 0.5 mol, and more preferably 0.08 to 0.2 mol, per mol of Compound (3).

Further, in the coupling step, a base (a reagent for activation of boron species) may be used in addition to the palladium catalyst. This base is not particularly limited insofar as the base is a compound that can form an ate complex on the boron atom by a Suzuki-Miyaura coupling reaction. More specifically, examples of bases include potassium fluoride, cesium fluoride, sodium hydroxide, potassium hydroxide, sodium methoxide, sodium hydrogen carbonate, potassium hydrogen carbonate, sodium carbonate, potassium carbonate, cesium carbonate, potassium phosphate, sodium acetate, potassium acetate, and calcium acetate. Among these, cesium fluoride, cesium carbonate and potassium phosphate are preferable. The amount of the base is generally about 0.1 to 5.0 mol, and preferably 0.5 to 1.0 mol, per mol of Compound (3).

Further, the reaction in the coupling step is generally performed in the presence of a reaction solvent. Examples of reaction solvents include aromatic hydrocarbons such as toluene, xylene, or benzene; esters such as methyl acetate, ethyl acetate, or butyl acetate; cyclic ethers such as diethylether, tetrahydrofuran, dioxane, or dimethoxyethane, diisopropylether; halogenated hydrocarbons such as methyl chloride, chloroform, dichloromethane, dichloroethane, or dibromoethane; ketones such as acetone, or methylethylketone; amides such as dimethylformamide or dimethylacetamide; nitriles such as acetonitrile; alcohols such as methanol, ethanol, or isopropylalcohol; and dimethylsulfoxides. These substances can be used singly or in a combination of two or more. Among them, tetrahydrofuran, etc., are preferable in the present invention.

The reaction temperature in the above coupling step is generally not less than 0° C., and is selected from a temperature range not more than the boiling point of the reaction solvent.

Further, the reaction atmosphere in the above coupling step is not particularly limited; an inert gas atmosphere, such as an argon gas atmosphere, a nitrogen gas atmosphere, etc., is preferable. It is also possible to adopt an air atmosphere.

3. Compounds (3) and (4)

Compound (3) includes Compound (3a) represented by General Formula (3a) below:

[Chem. 34]

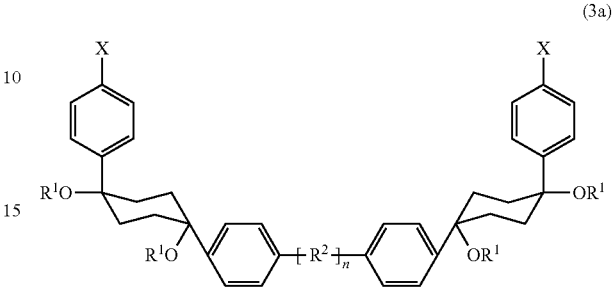

(3a)

wherein X, R$^1$, R$^2$ and n are as defined above, and Compound (3b) represented by General Formula (3b) below:

[Chem. 35]

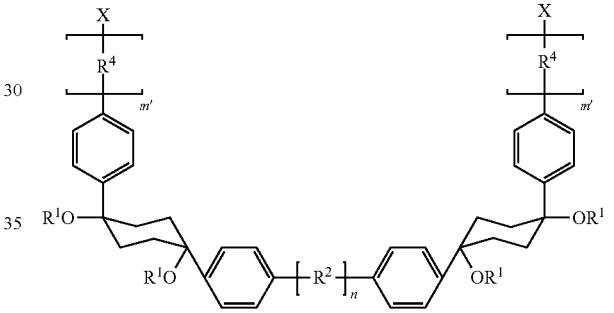

(3b)

wherein X, R$^1$, R$^2$, R$^4$ and n are as defined above; and m' is the same or different and each represents an integer of 1 or more.

Compound (3a)

Compound (3a) is an example of Compound (3) in which all of m are 0.

Further, in General Formula (3a), X and R$^1$ are as defined above in Reaction Formula 1, and R$^2$ and n are as defined above in General Formula (1).

Further, when General Formula (3a) has a structure in which n=1, the carbon atom of the bivalent organic ring group R$^2$ is bonded to the carbon atom of a phenylene group attached to a cyclohexylene group having two —OR$^1$ groups. Moreover, when n in General Formula (3a) is an integer of 2 or more, multiple R$^2$ are continuously bonded, and the two carbon atoms of R$^2$ at both ends are bonded to the carbon atom of the phenylene groups attached to the two cyclohexylene groups having two —OR$^1$ groups.

Compound (3a) has a structure in which each cyclohexylene group having two —OR$^1$ groups is adjacently disposed to each benzene ring having the halogen atom X. These cyclohexylenes are symmetrically positioned in Compound (3a). The benzene ring generally has a rigid plain structure. On the other hand, in the present invention, the cyclohexane ring of each cyclohexylene group is attached to the benzene ring at the 1-position and 4-position, forming a nonlinear (L-shaped) structure of chair conformation in which the benzene rings are respectively at axial and equatorial positions. Accordingly, the compound represented by General Formula (3a) generally has an overall U-shape.

Compound (3a) has the halogen atom X at each molecular terminus. Therefore, by using Compound (3a) as a reaction material, it is possible to produce Carbon Nanoring (1) and various compounds.

As described above, Carbon Nanoring (1) contains a compound in which organic ring groups such as cycloparaphenylene are circularly bonded. By using a U-shaped compound as Compound (3a), a compound having a cyclic structure can be more easily formed. Further, in Compound (3a), an arbitrary number of organic rings can be linked. Therefore, Compound (3a) is useful as a raw material for the production of carbon nanorings with specific diameters. More specifically, the use of Compound (3a) enables the production of carbon nanorings having various diameters and also makes it possible to accurately set the nanoring diameter.

Further, the cyclohexylene may be converted into phenyl group through a dehydrogenation reaction, an oxidation reaction, or the like. In particular, because Compound (3a) has a structure in which $OR^1$, such as a hydroxyl group, is disposed at each of the 1-position and 4-position of the cyclohexylene, it is possible to more efficiently convert cyclohexylene into phenyl group.

Further, by using Compound (3a), it is also possible to produce a compound in which the organic rings are connected like a chain.

For example, by reacting Compound (3a) with a compound having a boronic acid (or esters thereof) group at a terminus, it is possible to form a chain-like structure having, for example, a combination of U-shaped structures.

Method for Producing Compound (3a)

Compound (3a) can be produced through a reaction scheme represented by Reaction Formula 2 below:

Reaction Formula 2

[Chem. 36]

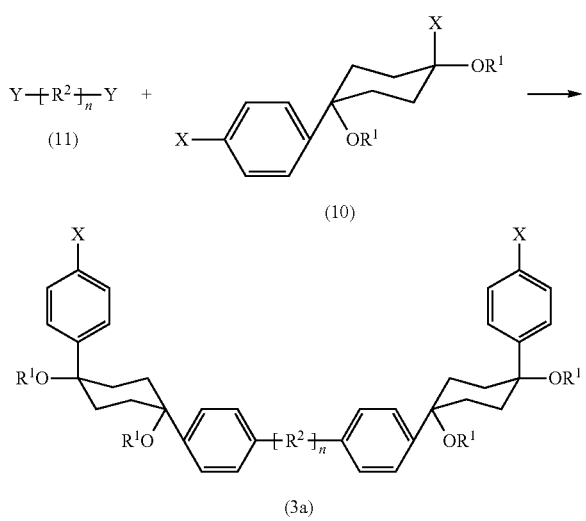

wherein X, Y, $R^1$, $R^2$ and n are as defined above.

This reaction step is described below.

Compound (3a) can be produced by a reaction step of reacting, in the presence of a palladium catalyst, Compound (10) represented by General Formula (10) below:

[Chem. 37]

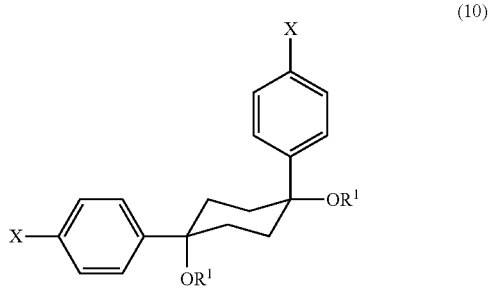

wherein X and $R^1$ are as defined above; and

Compound (11) represented by General Formula (11) below:

[Chem. 38]

wherein Y, $R^2$ and n are as defined above.

In the above reaction step, Compound (3a) can be produced by reacting Compound (10) and Compound (11). As in the aforementioned coupling step, a Suzuki-Miyaura coupling reaction can be adopted for this reaction of Compound (10) and Compound (11).

As in the Suzuki-Miyaura coupling reaction, a catalyst is used in the above reaction. In the present invention, a palladium catalyst is preferable.

Compound (10) has a 1,4-diphenylcyclohexane skeleton, and contains a halogen atom X at each terminus.

In General Formula (10), X and $R^1$ are as defined above in Reaction Formula 1.

In General Formula (10), the two Xs may be the same or different. Further, in General Formula (10), the two $R^1$ may be the same or different.

In General Formula (11), Y is as defined above in Reaction Formula 1, and $R^2$ and n are as defined above in General Formula (1).

Moreover, when n in General Formula (3a) is an integer of 2 or more, the corresponding number of $R^2$ may be the same or different.

Further, Y in General Formula (11) is the monovalent group (boronic acid (or esters thereof) group) shown in General Formula (9). In General Formula (11), the two Ys may be the same or different. In General Formula (9), the two $R^3$ may be the same or different. Further, when $R^3$ is alkyl group, the carbon atoms of these alkyl groups may be bonded to form a ring with the boron atom and the oxygen atoms.

Y in General Formula (9) is, for example, a group represented by one of Formulae (9a) to (9c) below:

[Chem. 39]

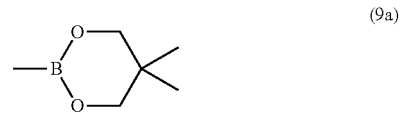

(9b)

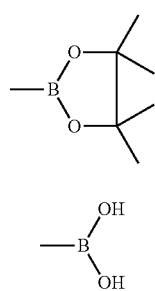

(9c)

When Y in General Formula (11) is a group represented by one of Formulae (9a) to (9c), the reaction of Compound (10) and Compound (11) can be more efficiently performed.

The amounts of Compound (10) and Compound (11) in the above reaction step are as follows in view of the yield of Compound (3a). The amount of Compound (11) is preferably 0.01 to 0.5 mol, more preferably 0.05 to 0.4 mol, and more preferably 0.08 to 0.2 mol, per mol of Compound (10).

As described above, this reaction step generally uses a palladium catalyst. The palladium catalyst can be selected from the palladium catalysts used in the above coupling reaction step. Pd(PPh$_3$)$_4$ and the like are particularly preferable.

The amount of the palladium catalyst is generally 0.0001 to 0.1 mol, preferably 0.0005 to 0.02 mol, and more preferably 0.001 to 0.01 mol, per mol of Compound (10), in terms of the yield.

Further, in the above reaction step, as required, it is possible to use a phosphorus ligand that can be coordinated with the palladium atom that is the center element of the palladium catalyst. This phosphorus ligand can be selected from the phosphorus ligands used in the above coupling reaction step. 2-(dicyclohexylphosphino-2',4',6'-tri-isopropyl-1,1'-biphenyl(X-Phos) and the like are particularly preferable.

When the phosphorus ligand is used, the amount is, in view of the yield, generally 0.001 to 1.0 mol, preferably 0.01 to 0.8 mol, and more preferably 0.05 to 0.3 mol, per mol of Compound (10).

Further, in the above reaction step, a base (a reagent for activation of boron species) is preferably used in addition to the palladium catalyst. This base can be selected from the bases used in the above coupling step. The amount of the base (reagent for activation of boron species) is generally 0.01 to 10 mol, preferably 0.1 to 5.0 mol, and more preferably 0.5 to 1.0 mol, per mol of Compound (10) used as a raw material.

The reaction in the above reaction step is generally performed in the presence of a reaction solvent. This reaction solvent can be selected from the reaction solvents used in the above coupling step.

The reaction temperature in the above reaction step is generally selected from a temperature range not less than 0° C. and not more than the boiling point of the reaction solvent.

Further, the reaction atmosphere in the above reaction step is not particularly limited; however, an inert gas atmosphere, such as an argon gas atmosphere, a nitrogen gas atmosphere, etc., is preferable. It is also possible to adopt an air atmosphere.

Compound (10) can be obtained, for example, by reacting 1,4-cyclohexanedione represented by Formula (12) below:

[Chem. 40]

(12)

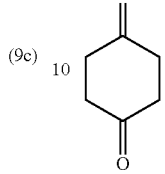

with a compound (which may also be referred to as an "aromatic dihalogen compound" hereinafter) represented by General Formula (13):

[Chem. 41]

(13)

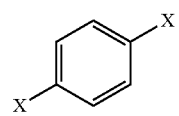

wherein X is as defined above.

X in General Formula (13) is as defined in Reaction Formula 1. The two Xs may be the same or different.

The aromatic dihalogen compound represented by General Formula (13) is not particularly limited insofar as the aromatic dihalogen compound has halogen atoms at the 1-position and 4-position. Examples of such compounds include 1,4-dibromobenzene, 1,4-diiodobenzene, and 1-bromo-4-iodobenzene.

When Compound (10) is produced in the above method, the amounts of 1,4-cyclohexanedione and the aromatic dihalogen compound represented by General Formula (13) are as follows. The amount of the aromatic dihalogen compound is preferably 2.0 to 10 mol, more preferably 2.3 to 5.0 mol, and still more preferably 2.5 to 3.5 mol, per mol of 1,4-cyclohexanedione.

The method for producing Compound (10) using the above raw material is not particularly limited. More specifically, the following method can be adopted. The aromatic dihalogen compound is reacted with an organic alkali metal compound to cause an interchange reaction of an alkali metal atom with a halogen atom, thereby obtaining a precursor compound containing a halogen atom and a hydrocarbon group in which a halogen atom of the aromatic dihalogen compound is substituted with a hydrocarbon group of the organic alkali metal compound; then, the resulting precursor compound is reacted with 1,4-cyclohexanedione to cause a nucleophilic addition reaction, thereby obtaining Compound (10). In this method, 1,4-dibromobenzene, 1,4-diiodobenzene, 1-bromo-4-iodobenzene, and the like are preferably used as the aromatic dihalogen compound.

Further, examples of the organic alkali metal compounds include organic lithium compounds and organic sodium compounds. Organic lithium compounds are particularly preferable. Examples of organic lithium compounds include organic monolithium compounds, organic dilithium compounds, and organic polylithium compounds.

Examples of organic lithium compounds include ethyllithium, n-propyllithium, isopropyllithium, n-butyllithium, sec-butyllithium, tert-butyllithium, pentyllithium, hexyllithium, cyclohexyllithium, phenyllithium, hexamethylene dilithium, cyclopentadienyl lithium, indenyl lithium, 1,1-diphenyl-n-hexyllithium, 1,1-diphenyl-3-methylpentyllithium, lithium naphthalene, butadienyl dilithium, isoprepenyl dilithium, m-diisoprenyl dilithium, 1,3-phenylene-bis-(3-methyl-1-phenylpentylidene)bislithium, 1,3-phenylene-bis-(3-methyl-1,[4-methylphenyl] pentylidene)bislithium, 1,3-phenylene-bis-(3-methyl-1,[4-dodecylphenyl] pentylidene) bislithium, 1,1,4,4-tetraphenyl-1,4-dilithio butane, polybutadienyl lithium, polyisoprenyl lithium, polystyrene butadienyl lithium, polystyrenyl lithium, polyethylenyl lithium, poly-1,3-cyclohexa dienyl lithium, polystyrene 1,3-cyclohexadienyl lithium, and polybutadiene 1,3-cyclohexadienyl lithium. Among these, n-butyllithium is preferable.

The amount of organic alkali metal compound is preferably 0.8 to 5 mol, more preferably 0.9 to 3.0 mol, and still more preferably 0.9 to 1.2 mol, per mol of the aromatic dihalogen compound represented by General Formula (13).

As the raw materials for the above method for producing Compound (10), it is preferable to use a combination of 1,4-dibromobenzene as the aromatic dihalogen compound and n-butyllithium as the organic alkali metal compound. In this case, the reaction of 1,4-dibromobenzene with n-butyllithium (a lithium-bromo interchange reaction) produces 4-bromophenyllithium. Then, by causing a nucleophilic addition reaction of 4-bromophenyllithium and cyclohexane 1,4-dione, the compound represented by Formula (10a) below:

[Chem. 42]

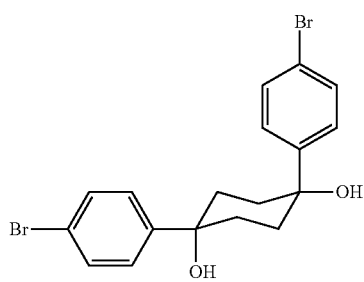

(10a)

is obtained.

Further, in the above reaction, a metal chloride, such as lithium chloride, cerium chloride, or the like, may be used. For example, when 1,4-dibromobenzene is used as the aromatic dihalogen compound and n-butyllithium is used as the organic alkali metal compound, 4-bromophenyllithium may be reacted, undesirably, as a base (side reaction). This is a common side reaction of an organic lithium reaction agent such as n-butyllithium or the like. To avoid such a side reaction, it is possible to prepare a corresponding 4-bromophenyl cerium reaction agent (an organocerium reaction agent) from 4-bromophenyllithium and cerium chloride in the above reaction system. This organic cerium reaction agent generally has low basicity, and thus is considered to suppress side reactions. Lithium chlorides can also be used, because lithium chlorides are considered to have an effect of increasing the solubility of, for example, a 4-bromophenylcerium reaction agent in organic solvents.

When a metal chloride, such as lithium chloride, cerium chloride, or the like, is used, the amount thereof is preferably 0.1 to 100 molar equivalents, and more preferably 0.5 to 20 molar equivalents, with respect to the aromatic dihalogen compound (in particular, 1,4-dibromobenzene).

The reaction of the aromatic dihalogen compound and the organic alkali metal compound is generally performed in the presence of a reaction solvent. The reaction solvent can be selected from those used in the above coupling step.

The temperature in the reaction of the aromatic dihalogen compound and the organic alkali metal compound is generally selected from a range not less than 0° C. and not more than the boiling point of the reaction solvent.

Further, the reaction atmosphere is not particularly limited; an inert gas atmosphere, such as an argon gas atmosphere, a nitrogen gas atmosphere, etc., is preferable. It is also possible to adopt an air atmosphere.

Further, in the process of producing Compound (3a), a purification step may be performed after the reaction step as necessary. Specifically, general post-treatment steps, such as solvent removal (when a solvent is used), washing, chromatography separation, or the like, may be performed.

Compound (3a) obtained by the present invention can be formed by reacting Compound (10) and Compound (11). Therefore, by appropriately setting the number "n" of $R^2$ in Compound (11), it is possible to arbitrarily and accurately design the number of organic rings, i.e., the length of Compound (3a). This enables accurate designing of the length of Compound (3a).

Compound (3b)

Compound (3b) is an example of Compound (3) in which all of m are m', which are equal to or more than 1. "m'" is the same as "m" except that it excludes 0. Thus, otherwise, "m'" is as defined in "m" in General Formula (1).

Further, in General Formula (3b), $R^1$ and X are as defined above in Reaction Formula 1, and $R^2$, $R^4$ and n are as defined above in General Formula (1).

Further, when General Formula (3b) has a structure in which n=1, the carbon atom of the bivalent organic ring group $R^2$ is bonded to the carbon atom of the phenylene group attached to the cyclohexylene group having two —$OR^1$ groups. Moreover, when n in General Formula (3a) is an integer of 2 or more, multiple $R^2$ are continuously bonded, and the two carbon atoms of $R^2$ at both ends are bonded to the carbon atom of the phenylene groups attached to the two cyclohexylene groups having two —$OR^1$ groups.

Compound (3b) has a structure in which each benzene ring is adjacent to a bivalent organic ring group having a halogen atom X, and each cyclohexylene group having two —$OR^1$ groups is adjacent to the benzene ring. These cyclohexylene groups are symmetrically positioned in Compound (3b). The benzene ring generally has a rigid plain structure. On the other hand, in the present invention, the cyclohexane ring of each cyclohexylene group is attached to the benzene ring at the 1-position and 4-position, forming a nonlinear (L-shaped) structure of chair conformation in which the benzene rings are respectively at axial and equatorial positions. Accordingly, the compound represented by General Formula (3b) generally has an overall U-shape.

Compound (3b) has the halogen atom X at each molecular terminus. Therefore, by using Compound (3b) as a reaction material, it is possible to produce Carbon Nanoring (1), various compounds, and the like.

As described above, Carbon Nanoring (1) is a compound in which organic ring groups such as cycloparaphenylene are circularly bonded. By using a U-shaped compound as Compound (3b), a compound having a cyclic structure can be more easily formed. Further, in Compound (3b), an arbitrary number of organic rings can be bonded. Therefore, Compound (3b) is useful as a raw material for the production of carbon nanorings with specific diameters. More specifically, the use of Compound (3b) enables the production of carbon nanorings having various diameters and also makes it possible to accurately set the nanoring diameter.

Further, the cyclohexylene group may be converted into phenyl through a dehydrogenation reaction, oxidation reaction, or the like. In particular, because Compound (3b) has a structure in which $OR^1$, such as a hydroxyl group, is disposed at each of the 1-position and 4-position of the cyclohexylene group, it is possible to more efficiently convert cyclohexylene group into phenyl group.

Further, by using Compound (3b), it is also possible to produce a compound in which the organic rings are connected like a chain.

For example, by reacting Compound (3b) with a compound having a boronic acid (or esters thereof) group at a terminus, it is possible to form a chain-like structure having, for example, a combination of U-shaped structures.

Compound (4)

Compound (4) is an example of Compound (3a) in which X is converted into Y.

Further, in General Formula (4), Y and $R^1$ are as defined above in Reaction Formula 1, and $R^2$, $R^4$ and n are as defined above in General Formula (1). Other characteristics of Compound (4) are the same as those of Compound (3a), except for X.

As described above, carbon nanorings can be produced by subjecting Compound (3) and Compound (4) to a coupling reaction.

Further, by subjecting Compound (3) and a compound other than Compound (4) having a boronic acid (or esters thereof) group at both ends to a coupling reaction, it is also possible to form a compound having a cyclic structure.

In particular, by using a cyclic compound obtained by subjecting Compound (3) and Compound (4') represented by Formula (4'):

[Chem. 43]

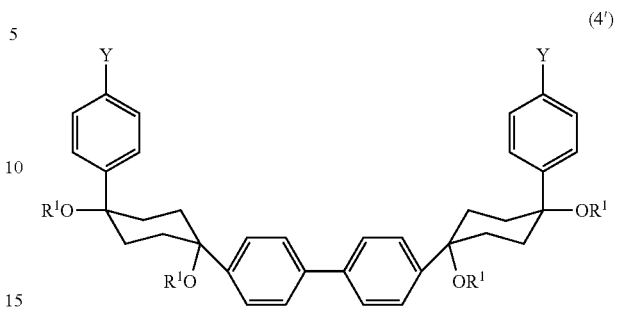

(4')

wherein Y and $R^1$ are as defined above, to a coupling reaction, it is possible to form a carbon nanoring wherein the total number of phenylene groups, $R^2$, and $R^4$ is 13 or more.

Further, by subjecting Compound (4) and a compound other than Compound (3) having a halogen atom in both ends to a coupling reaction, it is also possible to form a compound having a cyclic structure.

In particular, by using a cyclic compound obtained by subjecting Compound (4) and Compound (3') represented by Formula (3'):

[Chem. 44]

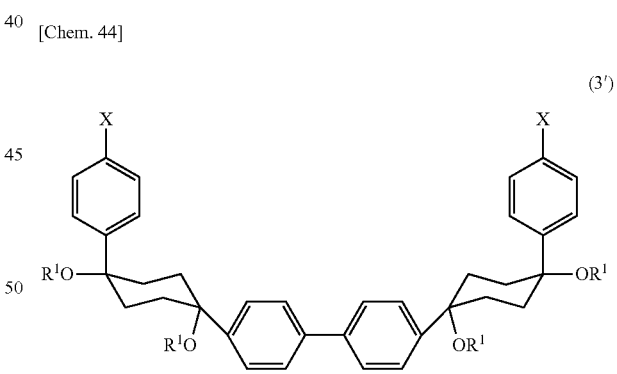

(3')

wherein X and $R^1$ are as defined above, to a coupling reaction, it is possible to form a carbon nanoring wherein the total number of phenylene groups, $R^2$, and $R^4$ is 13 or more.

Methods for Producing Compound (3B) and Compound (4), and Process to Obtain Compound (2)

Compound (2) is produced via various compounds (Compounds (3a) to (3c), and (4)) as shown in the scheme represented by Reaction Formula 3 below.

Reaction Formula 3

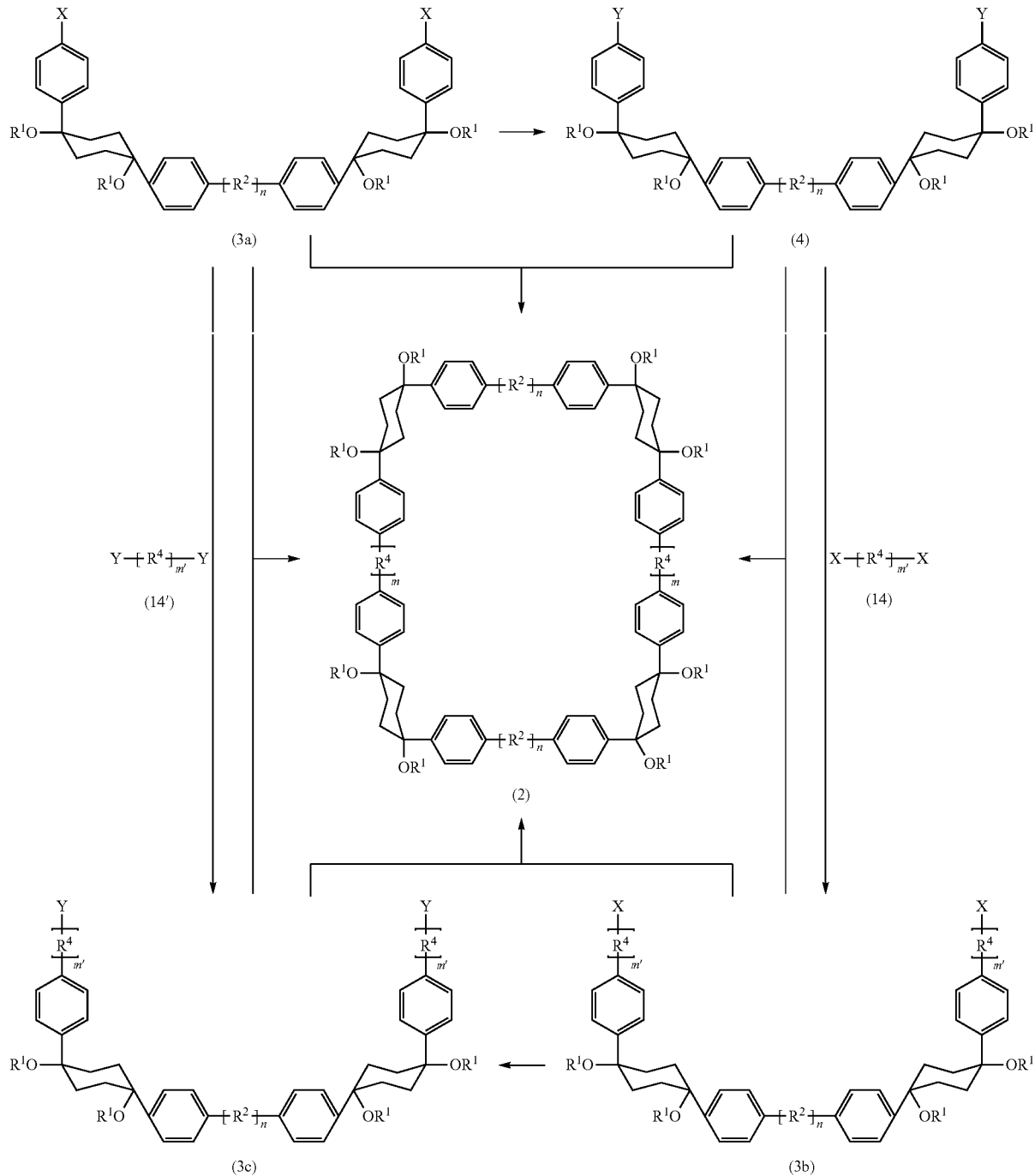

wherein X, Y, R¹, R², R⁴, n and m' are as defined above.

In particular, a process to obtain Compound (4) from Compound (3a) and a process to obtain Compound (3b) from Compound (4) are described below.

Modification Step (Production of Compound (4) from Compound (3a))

This modification step is a step for forming Compound (4) using Compound (3) and a boron compound having a boronic acid (or esters thereof) group (—B(OR³)$_2$; R³ is as defined above; this boron compound may be simply referred to as "boron compound" hereinafter).

In this modification step, the halogen atom X in Compound (3) is substituted with Y, which is a boronic acid (or esters thereof) group, in the boron compound, thereby obtaining Compound (4) having Y (boronic acid (or esters thereof) group) derived from the boron compound. This reaction for forming Compound (4) in this modification step is a borylation reaction.

Compound (3) used in the modification step is as defined above.

Further, Y (boronic acid (or esters thereof) group) in the boron compound is as defined in General Formula (9).

Examples of boron compounds used in the modification step include 2-phenyl-1,3,2-dioxaborinane, (4,4,5,5)-tetramethyl-1,3,2-dioxaborolane, 4,4,4',4',5,5,5',5'-octamethyl-2,2'-bi[1,3,2-dioxaborolane](bispinacolatodiboron), 5,5,5',5'-tetramethyl-5,5',6,6'-tetrahydro-2,2'-bi[4H-1,3,2-dioxaborine], and 1,1,2,2-tetrahydroxy-1,2-diboraethane.

The amount of the boron compound used in the modification step is preferably 1 to 10 mol, more preferably 1.5 to 7 mol, and still more preferably 2 to 5 mol, per mol of Compound (3).

The reaction in the modification step is generally performed in the presence of a catalyst, preferably a palladium catalyst. The palladium catalyst can be selected from the palladium catalysts used in the above coupling step. In this step, $Pd_2(dba)_3$, $Pd(PPh_3)_4$, and the like are preferable.

When a palladium catalyst is used in the modification step, the amount thereof is, in view of the yield, generally 0.001 to 1 mol, preferably 0.005 to 0.1 mol, and more preferably 0.01 to 0.05 mol, per mol of Compound (3) used as a raw material.

Further, in the modification step, a phosphorus ligand may be used together with a catalyst. This phosphorus ligand may be selected from the phosphorus ligands used in the coupling step. In this step, 2-(dicyclohexylphosphino)-2',4',6'-tri-isopropyl-1,1'-biphenyl(X-Phos) and the like are preferable.

When a phosphorus ligand is used in the modification step, the amount thereof is, in view of the yield, generally 0.01 to 1.0 mol, preferably 0.05 to 0.5 mol, and more preferably 0.08 to 0.2 mol, per mol of Compound (3) used as a raw material.

Further, as required, a base may be used in the modification step. The base may be selected from the bases used in the above coupling step. The amount of the base is generally about 0.1 to 5.0 mol, and preferably 0.5 to 1.0 mol, per mol of Compound (3) used as a raw material.

Further, the reaction in the modification step is generally performed in the presence of a reaction solvent. The reaction solvent may be selected from the reaction solvents used in the above coupling step.

The reaction temperature in the modification step is generally selected from a range of not less than 0° C. and not more than the boiling point of the reaction solvent.

Further, the reaction atmosphere in the modification step is not particularly limited; an inert gas atmosphere, such as an argon gas atmosphere, a nitrogen gas atmosphere, etc., is preferable. It is also possible to adopt an air atmosphere.

When the boron compound has a boronic acid ester group, it is possible to first produce Compound (4) having the boronic acid ester group, and then convert the boronic acid ester group into a boronic acid group through hydrolysis.

Step for Producing Compound (3B) from Compound (4)

This step forms Compound (3b) using Compound (4) and a dihalogen compound represented by General Formula (14) (which may also be referred to as "Dihalogen Compound (14)" hereinafter):

[Chem. 46]

$$X\text{—}[R^4]_{m'}\text{—}X \quad (14)$$

wherein X, $R^4$ and m' are as defined above.

In this step, Y (boronic acid (or esters thereof) group) in Compound (4) is substituted with $\text{—}[R^4]_{m'}\text{—}X$, thereby increasing the number of organic ring groups in the resulting Carbon Nanoring (1).

Compound (4) used in this step is as defined above.

Further, Y (boronic acid (or esters thereof) group) is as defined above in Reaction Formula 1.

Further, in General Formula (14), $R^4$ is as defined above in Carbon Nanoring (1) of the present invention, X is as defined above in Reaction Formula 1, and m' is as defined above in Compound (3b).

The amount of dihalogen compound (14) is preferably 0.1 to 10 mol, more preferably 0.5 to 5 mol, and still more preferably 0.8 to 2 mol, per mol of Compound (4).

The reaction in the modification step is generally performed in the presence of a catalyst, preferably a palladium catalyst. The palladium catalyst can be selected from the palladium catalysts used in the above coupling step. In this step, (1,1'-bis(diphenylphosphino)ferrocene)dichloropalladium(II), $Pd_2(dba)_3$, $Pd(PPh_3)_4$, and the like are preferable.

When a palladium catalyst is used in this step, the amount thereof is, in view of the yield, generally 0.001 to 1 mol, preferably 0.005 to 0.2 mol, and more preferably 0.01 to 0.1 mol, per mol of Compound (4) used as a raw material.

Further, in this step, a phosphorus ligand may be used with a catalyst. This phosphorus ligand may be selected from the phosphorus ligands used in the coupling step. In this step, 1,1'-bis(diphenylphosphino)ferrocene, 2-(dicyclohexylphosphino)-2',4',6'-tri-isopropyl-1,1'-biphenyl(X-Phos), and the like are preferable.

When a phosphorus ligand is used in this step, the amount thereof is, in view of the yield, generally 0.01 to 1.0 mol, preferably 0.05 to 0.5 mol, and more preferably 0.08 to 0.2 mol, per mol of Compound (4) used as a raw material.

Further, as required, a base may be used in this step. The base may be selected from the bases used in the above coupling step. In this step, sodium carbonate, potassium phosphate, and the like are preferable. The amount of the base is generally about 0.1 to 5.0 mol, and preferably 0.5 to 1.0 mol, per mol of Compound (4) used as a raw material.

Further, the reaction in the modification step is generally performed in the presence of a reaction solvent. The reaction solvent may be selected from the reaction solvents used in the above coupling reaction step. In this step, toluene, 1,4-dioxane, water, a mixed solvent thereof, and the like are preferable.

The reaction temperature in this step is generally selected from a range of not less than 0° C. and not more than the boiling point of the reaction solvent.

Further, the reaction atmosphere in the modification step is not particularly limited; an inert gas atmosphere, such as an argon gas atmosphere, a nitrogen gas atmosphere, etc., is preferable. It is also possible to adopt an air atmosphere.

As shown in Reaction Formula 1, Compound (2) can be produced by subjecting Compound (3) and Compound (4) to a coupling reaction. More specifically, as shown in Reaction Formula 3, Compound (2) can be produced through a coupling reaction of Compound (4) and Compound (3a) in which all of m' in Compound (3) are 0. Further, Compound (2) can be produced by subjecting Compound (4) and Compound (3b) in which all of m' in Compound (3) are equal to or more than 1 to a coupling reaction.

The method for producing Compound (2) is not limited to the above methods; Compound (2) can be produced in various ways.

For example, as shown in Reaction Formula 3, Compound (2) can also be produced through a coupling reaction of Compound (3a) in which all of m' in Compound (3) are 0, and Compound (3c) obtained by converting the two Xs in Compound (3b) into Ys. This reaction can be performed in the same manner as in the above coupling reaction of Compound (4) and Compound (3).

Further, as shown in Reaction Formula 3, Compound (2) can also be produced through a coupling reaction of Compound (3b) in which all of m' in Compound (3) are equal to or more than 1, and Compound (3c) obtained by converting the two Xs in Compound (3b) into Ys. This reaction can be performed in the same manner as in the above coupling reaction of Compound (4) and Compound (3).

Compound (3c) can be produced by reacting Compound (3b) and the boron compound having the boronic acid (or esters thereof) group (—B(OR$^3$)$_2$; R$^3$ is as defined above) in the presence of a palladium catalyst. This reaction can be performed in the same manner as in the above reaction for producing Compound (4) from Compound (3a). Further, Compound (3c) can be produced by reacting Compound (3a) and Compound (14') (Y—(R$^4$)$_{m'}$—Y, —Y; Y, R$^4$ and m' are as defined above) by converting —X in Compound (3a) into —(R$^4$)$_{m'}$—Y. This reaction can be performed in the same manner as in the above reaction for producing Compound (3b) from Compound (4).

[3] Embodiments

In the production of Compound (3), when Compound (11) represented by General Formula (11) in which R$^2$ is a naphthylene group (for example, the compound represented by Formula (11a) below):

[Chem. 47]

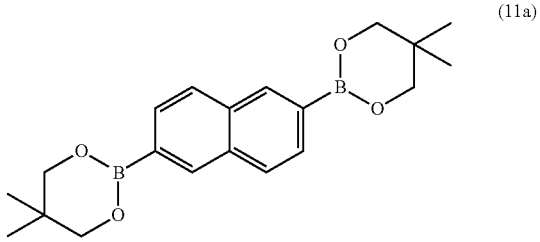
(11a)

is used, the compound represented by Formula (3a-1) below:

[Chem. 48]

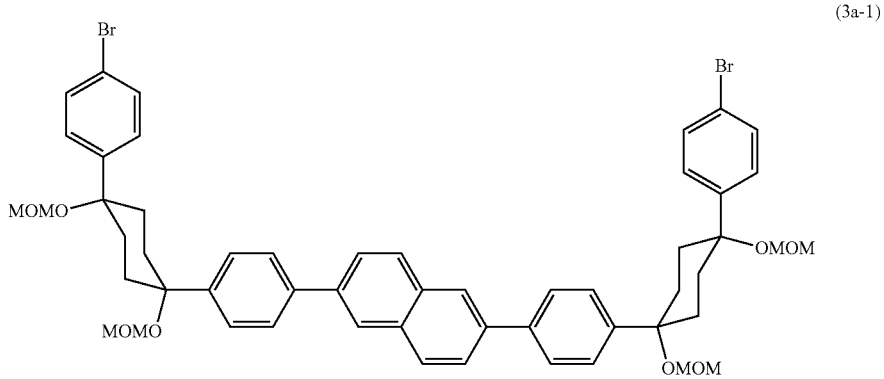
(3a-1)

is obtained.

Further, when a carbon nanoring is produced using the compound represented by Formula (3a-1) above, a cyclic compound represented by Formula (2a) below:

[Chem. 49]

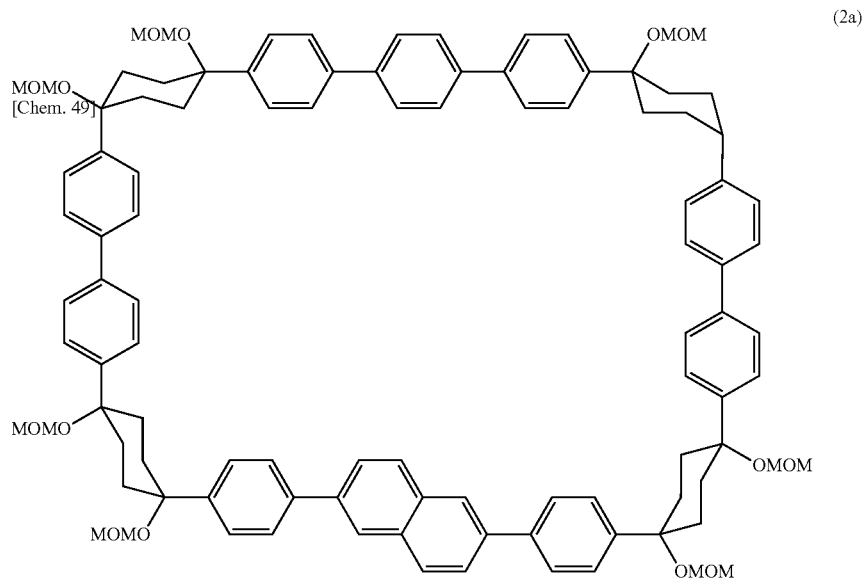
(2a)

is obtained through the above coupling step.

Furthermore, by subjecting the cyclic compound represented by Formula (2a) above to the above conversion step, the carbon nanoring represented by Formula (1b) below:

[Chem. 50]

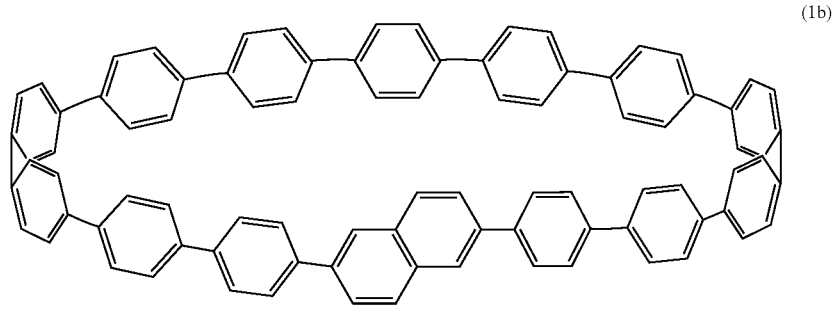

(1b)

is obtained. The carbon nanoring represented by Formula (1b) above contains a naphthylene group and 13 phenylene groups.

Further, as in the carbon nanoring represented by Formula (1b) above, when a part of the organic ring groups is, for example, a naphthylene group, a chiral carbon nanoring can be obtained. More specifically, the methods for producing compounds and carbon nanorings of the present invention enable the efficient production of chiral carbon nanorings (carbon nanotubes) having a specific number of organic rings.

Further, when Compound (14) represented by General Formula (14) wherein X is Br, $R^4$ is a pyridylidene group, and m' is 2 (for example, 5,5'-dibromo-2,2'-bipyridine represented by Formula (14a) below):

[Chem. 51]

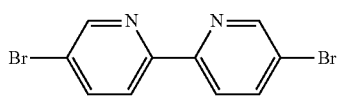

(14a)

is used for the production of Compound (3b), when $R^1$ is a methoxymethyl group, and $R^2$ is a phenylene group, the compound represented by Formula (3b-1) below:

[Chem. 52]

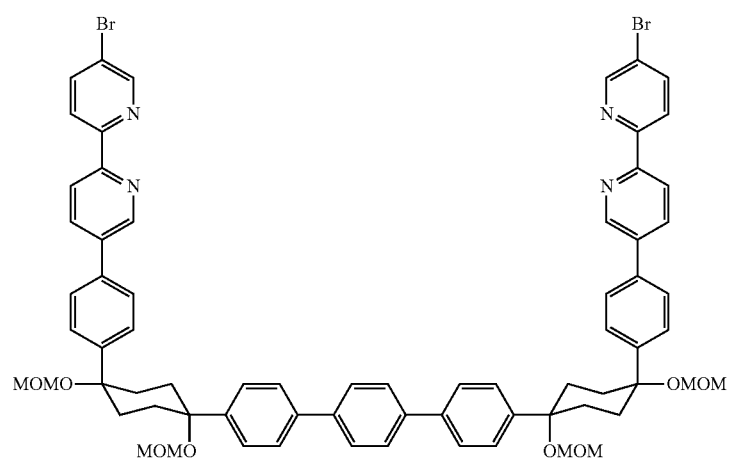

(3b-1)

is obtained.

Further, when a compound represented by Formula (3b-1) above and a compound represented by Formula (4a) below:
[Chem. 53]
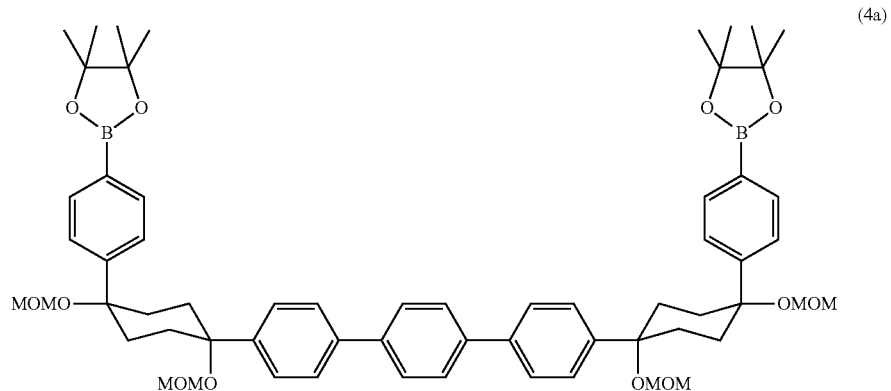
(4a)
are used in the production of a carbon nanoring, a cyclic compound represented by Formula (2b) below:
[Chem. 54]
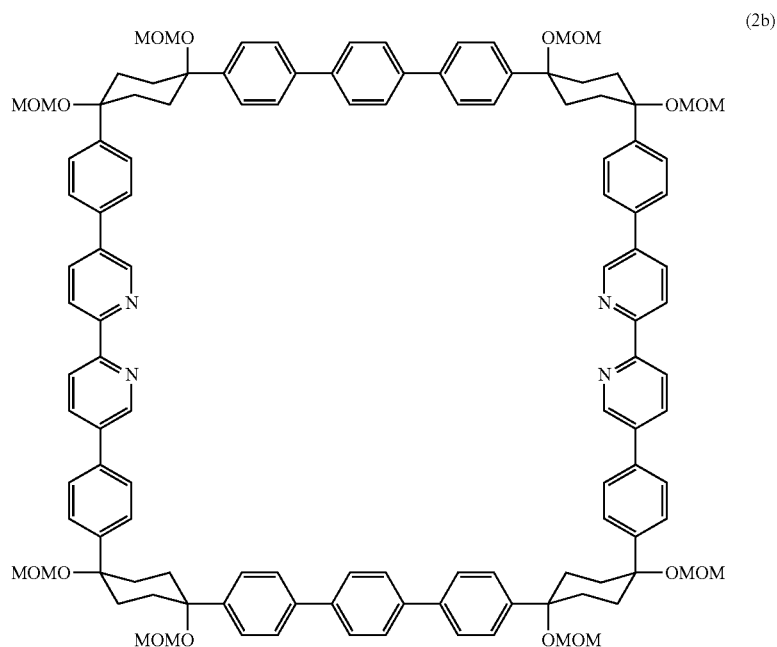
(2b)
is obtained through the above coupling step.

Furthermore, by subjecting the cyclic compound represented by Formula (2b) above to the above conversion step, the carbon nanoring (cyclo[14]para-phenylene[4]pyridylidene(CPPy)) represented by Formula (1c) below:

[Chem. 55]

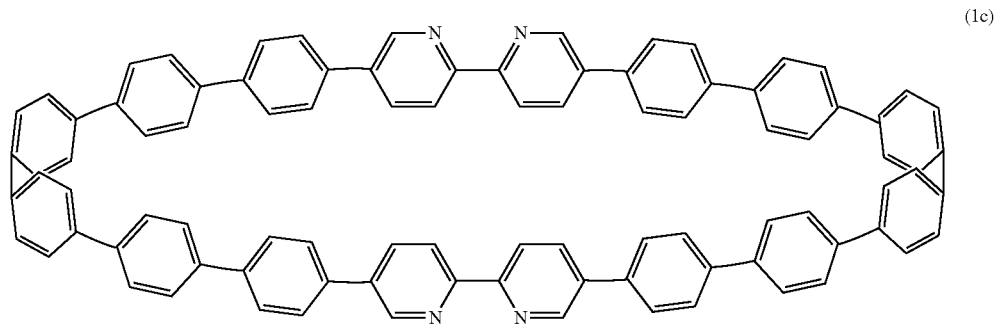

(1c)

is obtained. The carbon nanoring represented by Formula (1c) contains 4 pyridylidene groups and 14 phenylene groups.

Further, as in the carbon nanoring represented by Formula (1c) above, when a part of the organic ring groups is, for example, a pyridylidene group, a carbon nanoring containing a hetero atom is obtained. More specifically, the methods for producing compounds and carbon nanorings of the present invention enable the efficient production of hetero atom-containing carbon nanorings (carbon nanotubes) having a specific number of organic rings.

EXAMPLES

Hereinafter, the present invention is described in further detail with reference to Examples. However, the scope of the invention is not limited to these Examples. The NMR measurements in the Synthesis Examples and Examples were performed using a nuclear magnetic resonance spectrometer (model name: A-400) produced by JEOL Ltd.

Synthesis Example 1

Production of Compound (10a)

To a 1-L round-bottom flask were added lithium chloride (LiCl) (1.68 g, 33 mmol) and cerium(III)trichloride heptahydrate (14.4 g, 0.33 mol). The flask was immersed in an oil bath and heated at 90° C. for 2 hours under vacuum to dry. The obtained reactant mixture was crushed into a powder, and the powdered reactant mixture was returned to the flask. The flask was immersed again in an oil bath and heated at 90° C. for 1 hour under vacuum. A stirring bar was added to the flask, and the flask was immersed again in an oil bath and heated at 150° C. for 3 hours under vacuum while stirring. While the content in the flask was still hot, argon gas was introduced into the flask. Dry tetrahydrofuran (THF) (200 mL) was added thereto and the mixture was suspended. The resulting suspension was stirred at room temperature (i.e., about 23° C., the same applies hereinafter) for about 8 hours. A solution of cyclohexane-1,4-dione (1.68 g, 15 mmol) in THF (15 mL) was added to the suspension via a cannula. The mixture was stirred at room temperature for 2 hours and cooled to −78° C., thereby obtaining Suspension A.

To another 1-L round-bottom flask were added 1,4-dibromobenzene (10.7 g, 45 mmol) and dry THF (90 mL). A hexane solution of n-butyllithium (29.5 mL, 1.57 M, 45 mmol) was gradually added thereto dropwise at −78° C. (addition rate: 4.5 cm³/min). After completion of dropwise addition, the mixture was stirred at −78° C. for 30 minutes, and the resulting solution was added to Suspension A via a cannula, thereby obtaining a mixture.

The mixture was stirred at −78° C. for 1 hour, followed by stirring at room temperature for 2 hours. Thereafter, a saturated NH₄Cl aqueous solution (50 mL) was added to the mixture to stop the reaction. The resulting product was passed through Celite, and the filtrate was concentrated with an evaporator. Then, ethyl acetate was added to the residue (concentrate), the crude product was extracted and dried over anhydrous Na₂SO₄, and an ethyl acetate solution was thereby obtained. The solution was concentrated with an evaporator, and the residue (concentrate) was recrystallized from chloroform to yield a white solid (5.32 g). This white solid was identified by nuclear magnetic resonance (¹H-NMR, ¹³C-NMR) analysis and mass spectrometry as Compound (10a) represented by the following General Formula (10a):

[Chem. 56]

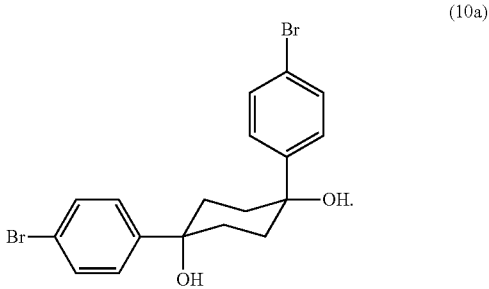

(10a)

The yield of Compound (10a) was 83%.

$^1$H NMR (270 MHz, CDCl$_3$) δ1.71 (s, 2H), d 2.07 (s, 8H), 7.34 (d, J=8.6 Hz, 4H), 7.47 (d, J=8.6 Hz, 4H); $^{13}$C NMR (67.5 MHz, CDCl$_3$) δ 33.2 (CH$_2$), 72.3 (4°), 121.5 (4°), 127.2 (CH), 131.6 (CH), 144.6 (4°); HRMS (FAB, negative) m/z calcd for C$_{18}$H$_{17}$Br$_2$O$_2$[M-H]$^-$: 422.9595, found 422.9576; mp: 177.7-178.7° C.

Synthesis Example 2

Introduction of Protecting Group to Hydroxyl Group of Compound (10a) Using Methoxymethyl Chloride To a 200-mL round-bottom flask containing a stirring bar were added Compound (10a) obtained in Synthesis Example 1 above (4.69 g, 11 mmol), dry dichloromethane (CH$_2$Cl$_2$) (44 mL), and diisopropylethylamine (7.7 mL, 44 mmol), and the flask was immersed in an ice bath. The mixture in the flask was stirred at 0° C. for 30 minutes, and methoxymethyl chloride (3.5 mL, 46 mmol) was then added thereto. After the mixture was reacted at room temperature for 18 hours while stirring, a saturated NH$_4$Cl aqueous solution (20 mL) was added to stop the reaction. The product was extracted with CH$_2$Cl$_2$ (20 mL×3), the organic phase from the extraction was dried over anhydrous Na$_2$SO$_4$, and a solution was obtained. The solution was concentrated with an evaporator, and the residue (concentrate) was purified by silica gel chromatography (CH$_2$Cl$_2$) to yield a colorless solid (5.48 g). This colorless solid was identified by nuclear magnetic resonance ($^1$H-NMR, $^{13}$C-NMR) analysis and mass spectrometry as Compound (10b) represented by the following General Formula (10b):

[Chem. 57]

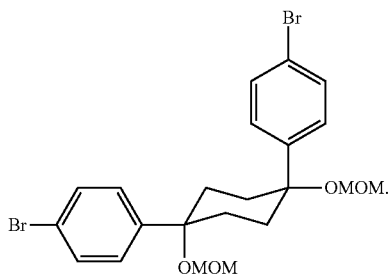

(10b)

The yield of Compound (10b) was 97%.

$^1$H NMR (270 MHz, CDCl$_3$) δ1.71 (s, 2H), 2.07 (s, 8H), 7.34 (d, J=9 Hz, 4H), 7.47 (d, J=9 Hz, 4H); $^{13}$C NMR (150 MHz, CDCl$_3$) δ 33.0 (CH$_2$), 56.2 (CH$_3$), 77.9 (4°), 92.3 (CH$_2$), 121.8 (4°), 128.7 (CH), 131.6 (CH), 141.6 (br, 4°); HRMS (FAB) m/z calcd for C$_{22}$H$_{26}$Br$_2$O$_4$Na [M+Na]$^+$: 535.0096, found 535.0103. mp: 107.1-108.9° C.

Synthesis Example 3

Production of Compound (11b) (1,4-benzenediboronic acid neopentyl glycol ester)

To a 50-mL round-bottom flask containing a stirring bar were added p-phenylenebisboronic acid (1,4-benzenediyl-bisboranic acid) (125 mg, 0.75 mmol, 1 equiv), neopentyl glycol (250 mg, 2.4 mmol, 3 equiv), p-toluenesulfonic acid (p-TsOH) (50 mg), and dry benzene (10 mL). The mixture was then reacted under reflux at 70° C. for 12 hours. After the mixture (reaction product) in the flask was cooled to room temperature, the target product was extracted with CH$_2$Cl$_2$. The organic phase from the extraction was washed with a saturated NaHCO$_3$ aqueous solution, and the solvent was then distilled off under reduced pressure to obtain a product (226.9 mg). This product was identified by nuclear magnetic resonance ($^1$H-NMR) analysis and mass spectrometry as a compound (1,4-benzenediboronic acid neopentyl glycol ester) represented by the following General Formula (11b):

[Chem. 58]

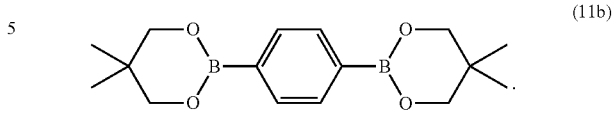

(11b)

This compound was referred to as (11b).

$^1$H NMR (270 MHz, CDCl$_3$) δ1.02 (s, 12H), 3.77 (s, 8H), 7.78 (s, 4H). LRMS (EI) m/z calcd for C$_{16}$H$_{24}$Br$_2$O$_4$[M]$^+$: 302.1861, found 302.

Compound (11c)

4,4'-Biphenyldiboronic acid neopentyl glycol ester

In Compound (11), 4,4'-biphenyldiboronic acid neopentyl glycol ester having a biphenylene group containing two benzene rings, represented by the following General Formula (11c), was used:

[Chem. 59]

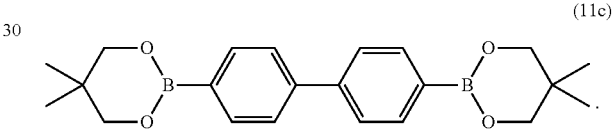

(11c)

This compound is commercially available.

Synthesis Example 4

Production of Compound (11a) Having Boronic Acid or Ester Thereof Group

To a 20-mL round-bottom flask containing a stirring bar were added 2,6-dibromonaphthalene (115.4 mg, 0.40 mmol), bis(neopentyl glycol)diboron (273.3 mg, 1.2 mmol), (1,1'-bis (diphenylphosphino)ferrocene)dichloropalladium(II) (10.3 mg, 13 μmol), and potassium acetate (KOAc) (244.8 mg, 2.5 mmol), and argon gas was introduced into the flask. Dry dimethylsulfoxide (2 mL) was added thereto, and the resulting mixture was reacted at 80° C. for 21 hours while stirring. Subsequently, the mixture (reaction product) in the flask was cooled to room temperature and passed through silica gel. After the solvent was distilled off from the filtrate under reduced pressure using an evaporator, the residue (concentrate) was recrystallized from hexane to yield a white solid (47.8 mg). This white solid was identified by nuclear magnetic resonance ($^1$H-NMR) analysis and mass spectrometry as a compound represented by the following General Formula (11a):

[Chem. 60]

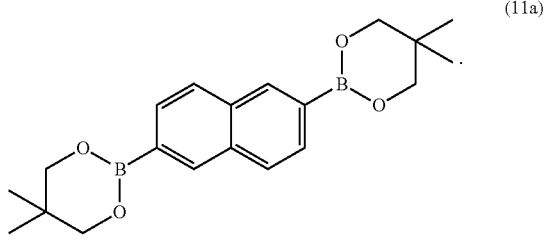

The yield of this compound was 31%. This compound was referred to as (11a).

$^1$H NMR (400 MHz, CDCl$_3$) δ1.06 (s, 12H), 3.83 (s, 8H), 7.83 (s, 4H), 8.33 (s, 2H). LRMS (EI) m/z calcd for C$_{20}$H$_{26}$B$_2$O$_4$ [M]$^+$: 352, found 352.

Example 1

Production of Compound (3a-2)

To a 200-mL round-bottom flask containing a stirring bar were added cesium fluoride (400 mg, 2.6 mmol), Compound (10b) obtained in Synthesis Example 2 (2.07 g, 4 mmol), Compound (11b) (1,4-benzenediboronic acid neopentyl glycol ester) obtained in Synthesis Example 3 (151.2 mg, 0.5 mmol), and [Pd(PPh$_3$)$_4$] (30.1 mg, 0.026 mmol), and argon gas was introduced into the flask. Dry THF (60 mL) was added thereto, and the resulting mixture was reacted at 65° C. for 26 hours while stirring. Subsequently, the mixture (reaction liquid) in the flask was cooled to room temperature and passed through Celite. After the solvent was distilled off from the resulting filtrate under reduced pressure using an evaporator, the residue (concentrate) was purified by silica gel chromatography (hexane/EtOAc) to yield a white solid (319.9 mg). This white solid was identified by nuclear magnetic resonance ($^1$H-NMR, $^{13}$C-NMR) analysis and mass spectrometry as a compound (hereinafter sometimes referred to as "Compound (3a-2)") represented by the following General Formula (3a-2):

The yield of Compound (3a-2) was 68%. Unreacted Compound (10b) (1.67 g) was also recovered through this purification process.

$^1$H NMR (400 MHz, CDCl$_3$) δ2.11 (brs, 8H), 2.30-2.40 (brm, 8H), 3.42 (s, 6H), 3.43 (s, 6H), 4.44 (s, 4H), 4.48 (s, 4H), 7.33 (d, J=9 Hz, 4H), 7.45 (d, J=9 Hz, 4H), 7.51 (d, J=9 Hz, 4H), 7.60 (d, J=9 Hz, 4H), 7.65 (s, 4H); $^{13}$C NMR (100 MHz, CDCl$_3$) δ 33.0 (CH$_2$), 56.0 (CH$_3$), 77.9 (4°), 78.1 (4°), 92.2 (CH$_2$), 92.3 (CH$_2$), 121.7 (4°), 126.9 (CH), 127.4 (CH), 128.7 (4°), 131.5 (CH), 139.5 (4°), 139.8 (4°); HRMS (FAB) m/z calcd for C$_{50}$H$_{56}$Br$_2$O$_8$Na [M$^+$Na]$^+$: 965.2240, found 965.2195; mp: 184.7-186.4° C.

Example 2

Production of Compound (3a-3)

To a 50-mL round-bottom flask containing a stirring bar were added cesium fluoride (165 mg, 1.1 mmol), Compound (10b) obtained in Synthesis Example 2 (521.3 mg, 1 mmol), the above-mentioned Compound (11c) (4,4'-biphenyldiboronic acid neopentyl glycol ester) (75.5 mg, 0.2 mmol), and [Pd(PPh$_3$)$_4$] (6.8 mg, 6 µmol), and argon gas was introduced into the flask. Dry THF (60 mL) was added thereto, and the resulting mixture was reacted at 65° C. for 26 hours while stirring. Subsequently, the mixture (reaction liquid) in the flask was cooled to room temperature and passed through Celite. After the solvent was distilled off from the resulting filtrate under reduced pressure using an evaporator, the residue (concentrate) was purified by silica gel chromatography (hexane/EtOAc) to yield a white solid (126.5 mg). This white solid was identified by nuclear magnetic resonance ($^1$H-NMR, $^{13}$C-NMR) analysis and mass spectrometry as a compound (hereinafter sometimes referred to as "Compound (3a-3)") represented by the following General Formula (3a-3):

[Chem. 61]

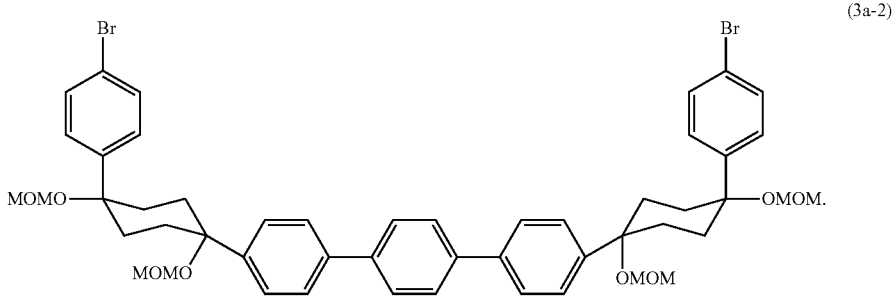

[Chem. 62]

(3a-3)

The yield of Compound (3a-3) was 62%. Unreacted Compound (10b) (279.1 mg) was also recovered through this purification process.

$^1$H NMR (400 MHz, CDCl$_3$) δ2.11 (brs, 8H), 2.34-2.37 (brm, 8H), 3.41 (s, 6H), 3.43 (s, 6H), 4.44 (s, 4H), 4.48 (s, 4H), 7.33 (d, J=9 Hz, 4H), 7.45 (d, J=9 Hz, 4H), 7.51 (d, J=9 Hz, 4H), 7.60 (d, J=9 Hz, 4H), 7.65 (s, 4H); $^{13}$C NMR (100 MHz, CDCl$_3$) δ 33.0 (CH$_2$), 56.0 (CH$_3$), 77.2 (4°), 77.9 (4°), 78.1 (4°), 92.2 (CH$_2$), 92.3 (CH$_2$), 121.7 (4°), 126.9 (CH), 127.4 (CH), 128.7 (4°), 131.5 (CH), 139.5 (4°), 139.8 (4°); HRMS (FAB) m/z calcd for C$_{56}$H$_{60}$Br$_2$O$_8$Na [M$^+$Na]$^+$: 1041.2553, found 1041.2532.

Example 3

Production of Compound (3a-1) (Part 1)

To a 50-mL round-bottom flask containing a stirring bar were added cesium fluoride (80.2 mg, 0.53 mmol), Compound (10b) obtained in Synthesis Example 2 (349.7 mg, 0.68 mmol), Compound (11a) obtained in Synthesis Example 4 (32.0 mg, 84 μmol), and [Pd(PPh$_3$)$_4$] (4.7 mg, 4 μmol), and argon gas was introduced into the flask. Dry THF (60 mL) was added thereto, and the resulting mixture was reacted at 60° C. for 24 hours while stirring. Subsequently, the mixture (reaction liquid) in the flask was cooled to room temperature and passed through Celite. After the solvent was distilled off from the resulting filtrate under reduced pressure using an evaporator, the residue (concentrate) was purified by silica gel chromatography (hexane/EtOAc) to yield a white solid (66.1 mg). This white solid was identified by nuclear magnetic resonance ($^1$H-NMR) analysis and mass spectrometry as a compound (hereinafter sometimes referred to as "Compound (3a-1)") represented by the following General Formula (3a-1):

[Chem. 63]

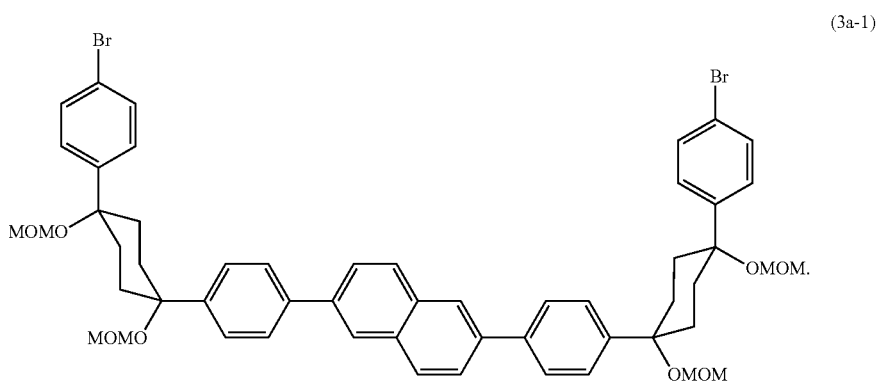

(3a-1)

The yield of Compound (3a-1) was 79%. Unreacted Compound (10b) (279.6 mg) was also recovered through this purification process.

$^1$H NMR (400 MHz, CDCl$_3$) δ2.13 (brs, 8H), 2.36 (brs, 8H), 3.42 (s, 6H), 3.44 (s, 6H), 4.44 (s, 4H), 4.50 (s, 4H), 7.33 (d, J=8.3 Hz, 4H), 7.45 (d, J=8.5 Hz, 4H), 7.54 (d, J=8.3 Hz, 4H) 7.71 (d, J=8.3 Hz, 4H), 7.74 (d, J=8.6 Hz, 4H), 7.94 (d, J=8.3 Hz, 2H), 8.03 (s, 2H). LRMS (FAB) m/z calcd for C$_{54}$H$_{58}$Br$_2$O$_8$[M]$^+$: 994.2478, found 994.

Synthesis Example 5

Production of Compound (4a) (Borylated Product)

To a 50-mL round-bottom flask containing a stirring bar were added Compound (3a-2) obtained in Example 1 (285.4 mg, 0.30 mmol), [Pd$_2$(dba)$_3$] (6.0 mg, 6.6 μmol), 2-(dicyclohexylphosphino)-2',4',6'-tri-isopropyl-1,1'-biphenyl (hereinafter sometimes referred to as "X-Phos") (13.3 mg, 28 μmol), bis(pinacolate)diboron (227.5 mg, 0.9 mmol), and potassium acetate (KOAc) (180.1 mg, 1.8 mmol), and argon gas was introduced into the flask. Dry dioxane (1,4-dioxane) (15 mL) was added thereto, and the resulting mixture was reacted at 90° C. for 5 hours while stirring. The resulting mixture (reaction liquid) in the flask was cooled to room temperature and passed through silica gel. After the solvent was distilled off from the resulting filtrate under reduced pressure using an evaporator, the residue (concentrate) was purified by gel permeation chromatography (chloroform) to yield a white solid (271.7 mg). This white solid was identified by nuclear magnetic resonance ($^1$H-NMR, $^{13}$C-NMR) analysis and mass spectrometry as a compound (hereinafter sometimes referred to as "Compound (4a)") represented by the following General Formula (4a):

[Chem. 64]

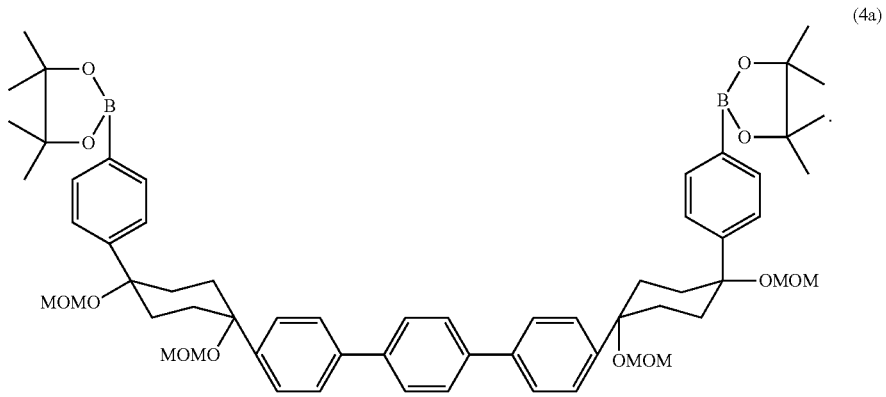

The yield of Compound (4a) was 87%.

$^1$H NMR (400 MHz, CDCl$_3$) δ1.32 (s, 24H) 2.14 (brs, 8H), 2.36 (brs, 8H), 3.41 (s, 6H), 3.43 (s, 6H), 4.43 (s, 4H), 4.48 (s, 4H), 7.46 (d, J=8 Hz, 2H), 7.49 (d, J=9 Hz, 2H), 7.45 (6, J=9 Hz, 4H), 7.51 (d, J=8 Hz, 4H), 7.60 (d, J=8.5 Hz, 4H), 7.65 (s, 4H); $^{13}$(NMR (100 MHz, CDCl$_3$) δ24.9 (CH$_3$), 33.0 (CH$_2$), 56.0 (CH$_3$), 78.2 (4°), 78.3 (4°), 83.8 (4°), 92.2 (CH$_2$), 92.3 (CH$_2$), 126.2 (4°), 126.9 (CH), 127.4 (CH), 134.8 (4°), 134.9 (CH), 139.5 (4°), 139.7 (4°); HRMS (FAB) m/z calcd for C$_{62}$H$_{80}$B$_2$O$_{12}$Na [M$^+$Na]$^+$: 1061.5753, found 1061.5719; mp: 225.1-226.6° C.

Synthesis Example 6

Production of Compound (4b) (Borylated Product)

To a 50-mL round-bottom flask containing a stirring bar were added Compound (3a-3) obtained in Example 2 (137 mg, 134 µmol), [Pd$_2$(dba)$_3$] (2.8 mg, 3.1 µmol), bis(pinacolate)diboron) (106 mg, 419 µmol), and potassium acetate (KOAc) (75.7 mg, 771 µmol), and argon gas was introduced into the flask. Dry dioxane (1,4-dioxane) (5 mL) was added thereto, and the resulting mixture was reacted at 90° C. for 5 hours while stirring. The resulting mixture (reaction liquid) in the flask was cooled to room temperature and passed through silica gel (EtOAc). After the solvent was distilled off from the resulting filtrate under reduced pressure using an evaporator, the residue (concentrate) was purified by gel permeation chromatography to yield a white solid (119 mg). This white solid was identified by nuclear magnetic resonance ($^1$H-NMR, $^{13}$C-NMR) analysis and mass spectrometry as a compound (hereinafter sometimes referred to as "Compound (4b)") represented by the following General Formula (4b):

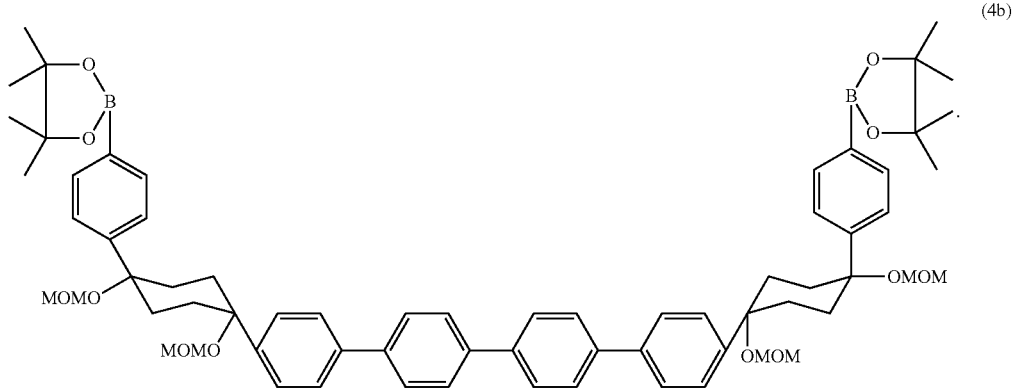

(4b)

The yield of Compound (4b) was 87%.

$^1$H NMR (400 MHz, CDCl$_3$) δ1.32 (s, 24H) 2.15 (brs, 8H), 2.37 (brs, 8H), 3.41 (s, 6H), 3.44 (s, 6H), 4.43 (s, 4H), 4.49 (s, 4H), 7.47 (d, J=8 Hz, 2H), 7.50 (d, J=8 Hz, 2H), 7.60 (6, J=9 Hz, 4H), 7.70 (d, J=9 Hz, 4H), 7.60 (d, J=8.5 Hz, 4H), 7.78 (d, J=8 Hz, 2H); $^{13}$C NMR (100 MHz, CDCl$_3$) δ 24.9 (CH$_3$), 33.0 (CH$_2$), 33.1 (CH$_2$) 56.1 (CH$_3$), 77.1 (4°), 78.3 (4°), 78.4 (4°), 83.9 (4°), 92.3 (CH$_2$), 126.3 (CH), 127.0 (CH), 127.4 (CH), 127.5 (CH), 134.9 (CH), 139.6 (4°), 139.7 (4°), 139.8 (4°); HRMS (FAB) m/z calcd for C$_{56}$H$_{60}$Br$_2$O$_8$Na [M+Na]$^+$: 1041.2553, found 1041.2532.

Example 4

Production of Cyclic Compound (2c) Containing 14 Organic Rings

To a 50-mL round-bottom flask containing a stirring bar were added Compound (3a-2) obtained in Example 1 (19.7 mg, 21 μmol), Compound (4a) obtained in Synthesis Example 5 (29.1 mg, 28 μmol), [Pd(OAc)$_2$] (0.9 mg, 4.0 μmol), and X-Phos (2.0 mg, 4.2 μmol), and argon gas was introduced into the flask. Dry dioxane (1,4-dioxane) (10 mL) and 10 M sodium hydroxide (NaOH) aqueous solution (18 mL, 0.18 mmol) were added thereto to obtain a mixture. The resulting mixture was reacted at 80° C. for 24 hours while stirring. Thereafter, the mixture (reaction liquid) in the flask was cooled to room temperature and passed through silica gel. After the solvent was distilled off from the resulting filtrate under reduced pressure using an evaporator, the residue (concentrate) was purified by silica gel chromatography (CHCl$_3$/EtOAc=1/1) to yield a white solid (14.6 mg). This white solid was identified by nuclear magnetic resonance ($^1$H-NMR) analysis and mass spectrometry as a cyclic compound in which 14 rings including phenylene groups and cyclohexylene derivative groups were continuously linked (hereinafter sometimes referred to as "Cyclic Compound (2c)"), the compound being represented by the following General Formula (2c):

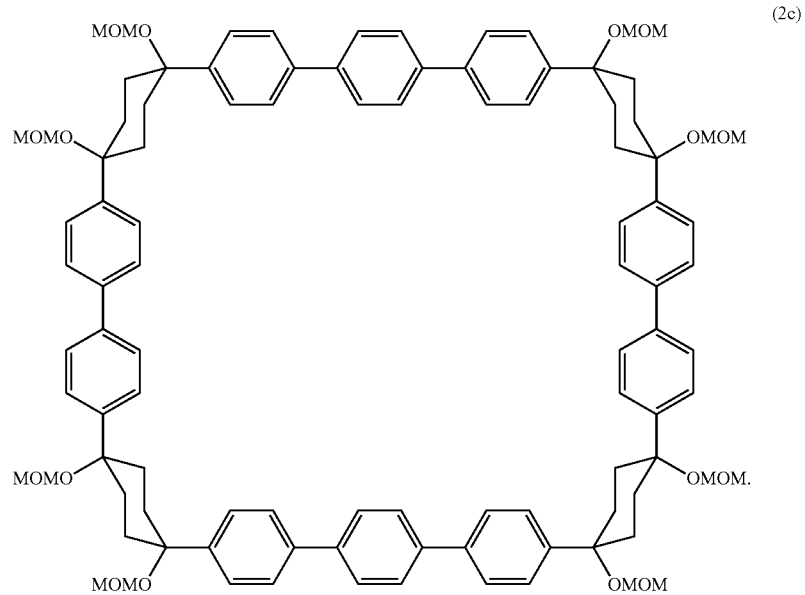

(2c)

The yield of Cyclic Compound (2c) was 45%.
$^1$H NMR (600 MHz, CDCl$_3$) δ2.18 (brs, 16H), 2.39 (brs, 16H), 3.42 (s, 12H), 3.43 (s, 12H), 4.46 (s, 8H), 4.48 (s, 8H), 7.57 (m, 40H). LRMS (FAB) m/z calcd for C$_{100}$H$_{112}$O$_{16}$ [M]$^+$: 1569.7984, found 1570.

Example 5

Production of Carbon Nanoring (1d) Made of Cycloparaphenylene Containing 14 Benzene Rings (Part 1)

To a 2-mL glass vial containing a stirring bar were added Cyclic Compound (2c) obtained in Example 4 (9.1 mg, 5.0 μmol), 0.1 M p-toluenesulfonic acid aqueous solution (50 μL, 5.0 μmol), and dry xylene (m-Xylene) (1 mL), thereby obtaining a mixture. This vial was placed in a microwave reactor (Initiator Synthesis System, produced by Biotage), and a reaction was carried out at 150° C. for 30 minutes while stirring. Subsequently, the mixture (reaction liquid) in the vial was cooled to room temperature and passed through silica gel. After the solvent was distilled off from the resulting filtrate under reduced pressure using an evaporator, the residue (concentrate) was purified by silica gel chromatography (CH$_2$Cl$_2$/hexane) to yield a white solid (1.1 mg). This white solid was identified by nuclear magnetic resonance ($^1$H-NMR) analysis and mass spectrometry as [14] cycloparaphenylene (amorphous) containing 14 benzene rings, represented by the following General Formula (1d):

[Chem. 67]

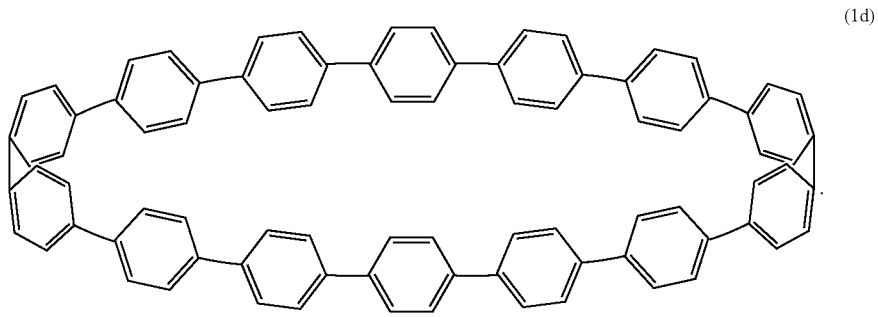

(1d)

The yield of [14] cycloparaphenylene was 20%.
$^1$H NMR (600 MHz CDCl$_3$) δ7.65 (s, 56H). MS (MALDI-TOF) m/z calcd for C$_{84}$H$_{56}$ [M]$^+$: 1064.4382, found 1064.424.

Example 6

Production of Carbon Nanoring (1d) Made of Cycloparaphenylene Containing 14 Benzene Rings (Part 2)

To a 20-mL Schlenk flask containing a stirring bar were added Cyclic Compound (2c) obtained in Example 4 (7.9 mg, 5.0 μmol), sodium hydrogen sulfate monohydrate (15.4 mg, 11.3 μmol), dry xylene (m-Xylene) (1 mL), and dry dimethylsulfoxide (DMSO) (1 mL), thereby obtaining a mixture. The mixture was reacted at 150° C. for 48 hours while stirring. Subsequently, the mixture (reaction liquid) in the Schlenk flask was cooled to room temperature and extracted with CHCl$_3$. After the organic phase from the extraction was dried over Na$_2$SO$_4$, the solvent was distilled off under reduced pressure to yield a crude product. The crude product was purified by silica gel preparative thin layer chromatography (CH$_2$Cl$_2$/hexane) to yield a white solid (2.0 mg). This white solid was identified by nuclear magnetic resonance ($^1$H-NMR, $^{13}$C-NMR) analysis and mass spectrometry as [14] cycloparaphenylene (amorphous) containing 14 benzene rings, represented by General Formula (1d) above. The yield of [14] cycloparaphenylene was 37%.
$^1$H NMR (600 MHz, CDCl$_3$) δ7.65 (s, 56H); $^{13}$C NMR (98.5 MHz, CDCl$_3$) δ 127.4 (CH), 138.8 (4°); HRMS (MALDI-TOF) m/z calcd for C$_{84}$H$_{56}$ [M]$^+$: 1064.4382, found 1064.438.

Example 7

Production of Cyclic Compound (2d) Containing 15 Organic Rings

To a 50-mL round-bottom flask containing a stirring bar were added Compound (3a-3) obtained in Example 2 (20.0 mg, 20 μmol), Compound (4a) obtained in Synthesis Example 5 (285.4 mg, 29 μmol), [Pd(OAc)$_2$] (1.0 mg, 4.4 μmol), and X-Phos (2.2 mg, 4.6 μmol), and argon gas was introduced into the flask. Dry dioxane (1,4-dioxane) (20 mL) and 10 M NaOH aqueous solution (19 mL, 0.19 mmol) were added thereto, and the resulting mixture was reacted at 80° C. for 24 hours while stirring. Thereafter, the mixture (reaction liquid) in the flask was cooled to room temperature and passed through silica gel. After the solvent was distilled off from the resulting filtrate under reduced pressure using an evaporator, the residue (concentrate) was purified by silica gel chromatography (CHCl$_3$/EtOAc=1/1) to yield a white solid (10.4 mg). This white solid was identified by nuclear magnetic resonance ($^1$H-NMR) analysis and mass spectrometry as a cyclic compound in which 15 rings including phenylene groups and cyclohexylene derivative groups were continuously linked (hereinafter sometimes referred to as "Cyclic Compound (2d)"), the compound being represented by the following General Formula (2d):

[Chem. 68]

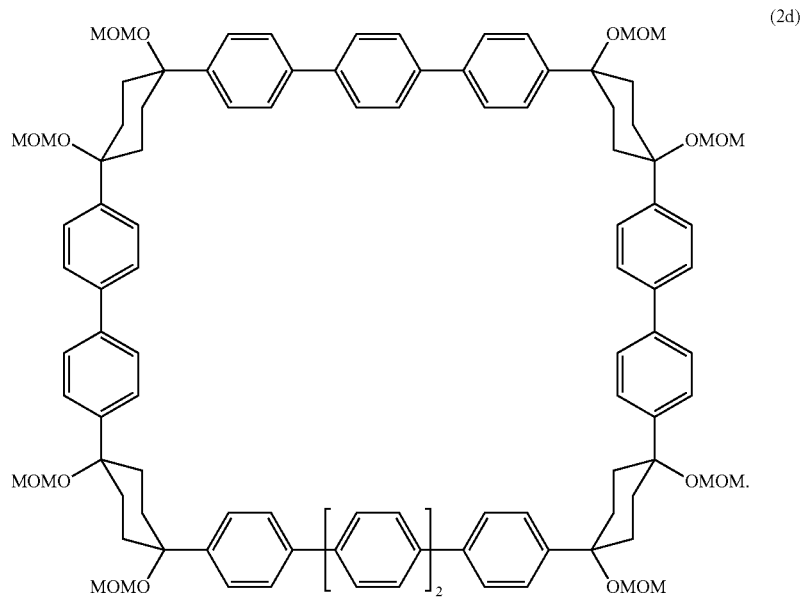

(2d)

The yield of Cyclic Compound (2d) was 32%.

$^1$H NMR (400 MHz, CDCl$_3$) δ2.18 (brs, 16H), 2.39 (brs, 16H), 3.44 (m, 24H), 4.48 (m, 16H), 7.57 (m, 44H). HRMS (FAB) m/z calcd for C$_{106}$H$_{116}$O$_{16}$ [M]$^+$: 1645.8297, found 1646.

Example 8

Production of Carbon Nanoring (1e) Made of Cycloparaphenylene Containing 15 Benzene Rings (Part 1)

To a 2-mL glass vial containing a stirring bar were added Cyclic Compound (2d) obtained in Example 6 (9.8 mg, 6.0 μmol), 0.1 M p-toluenesulfonic acid aqueous solution (120 μL, 12 μmol), and dry xylene (m-Xylene) (1 mL). The vial containing the resulting mixture was placed in a microwave reactor as in Example 5, and a reaction was carried out at 150° C. for 30 minutes while stirring. Subsequently, the mixture (reaction liquid) in the vial was cooled to room temperature and passed through silica gel. After the solvent was distilled off from the resulting filtrate under reduced pressure using an evaporator, the residue (concentrate) was purified by silica gel chromatography (CH$_2$Cl$_2$/hexane) to yield a white solid (0.5 mg). This white solid was identified by nuclear magnetic resonance ($^1$H-NMR) analysis and mass spectrometry as [15] Cycloparaphenylene (amorphous) containing 15 benzene rings, represented by the following General Formula (1e):

[Chem. 69]

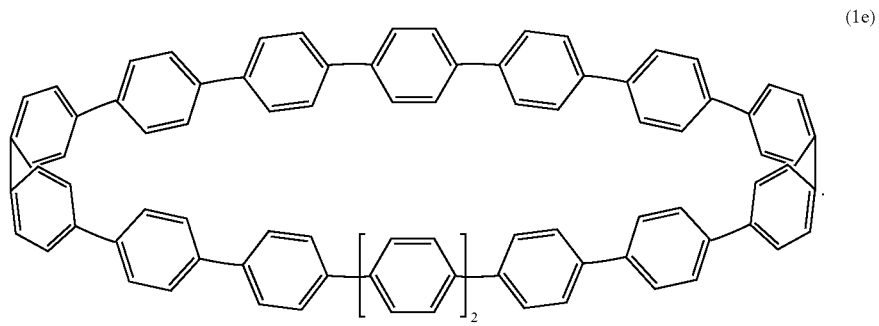

(1e)

The yield of [15] Cycloparaphenylene was 7%.

$^1$H NMR (400 MHz CDCl$_3$) δ7.67 (s, 60H). MS (MALDI-TOF) m/z calcd for C$_{90}$H$_{60}$ [M]$^+$: 1140.4695, found 1140.513.

Example 9

Production of Carbon Nanoring (1e) Made of Cycloparaphenylene Containing 15 Benzene Rings To a 20-mL Schlenk flask containing a stirring bar were added Cyclic Compound (2d) obtained in Example 6 (7.4 mg, 4.5 μmol), sodium hydrogen sulfate monohydrate (14.7 mg, 10.6 μmol), dry xylene (m-Xylene) (1 mL), and dry dimethylsulfoxide (DMSO) (1 mL). The resulting mixture was reacted at 150° C. for 48 hours while stirring. Subsequently, the mixture (reaction liquid) in the Schlenk flask was cooled to room temperature and extracted with CHCl$_3$. After the organic phase from the extraction was dried over Na$_2$SO$_4$, the solvent was distilled off under reduced pressure to yield a crude product. The crude product was purified by silica gel preparative thin layer chromatography (CH$_2$Cl$_2$/hexane) to yield a white solid (2.2 mg). This white solid was identified by nuclear magnetic resonance ($^1$H-NMR, $^{13}$C-NMR) analysis and mass spectrometry as [15] cycloparaphenylene (amorphous) containing 15 benzene rings, represented by General Formula (1e) above. The yield of [15] cycloparaphenylene was 43%.

$^1$H NMR (600 MHz, CDCl$_3$) δ7.67 (s, 60H); $^{13}$C NMR (150 MHz, CDCl$_3$) δ 127.3 (CH), 138.8 (4°); HRMS (MALDI-TOF) m/z calcd for C$_{90}$H$_{60}$ [M]$^+$: 1140.4695, found 1140.469.

Example 10

Production of Cyclic Compound (2e) Containing 16 Organic Rings

To a 50-mL round-bottom flask containing a stirring bar were added Compound (3a-3) obtained in Example 2 (42.8 mg, 38.0 μmol), Compound (4b) obtained in Synthesis Example 6 (26.7 mg, 26.2 μmol), [Pd(OAc)$_2$] (1.3 mg, 5.7 μmol), and X-Phos (6.9 mg, 14.4 μmol), and argon gas was introduced into the flask. Dry dioxane (1,4-dioxane) (13.5 mL) and 10 M NaOH aqueous solution (27.0 μL, 270 μmol) were added thereto, and the resulting mixture was reacted at 80° C. for 24 hours while stirring. Thereafter, the mixture (reaction liquid) in the flask was cooled to room temperature and passed through silica gel (EtOAc). After the solvent was distilled off from the resulting filtrate under reduced pressure using an evaporator, the residue (concentrate) was purified by silica gel preparative thin layer chromatography (CHCl$_3$: EtOAc=1:1) to yield a white solid (15.5 mg). This white solid was identified by nuclear magnetic resonance ($^1$H-NMR, $^{13}$C-NMR) analysis and mass spectrometry as a cyclic compound in which 16 rings including phenylene groups and cyclohexylene derivative groups were continuously linked (hereinafter sometimes referred to as "Cyclic Compound (2e) "), the compound being represented by the following General Formula (2e):

[Chem. 70]

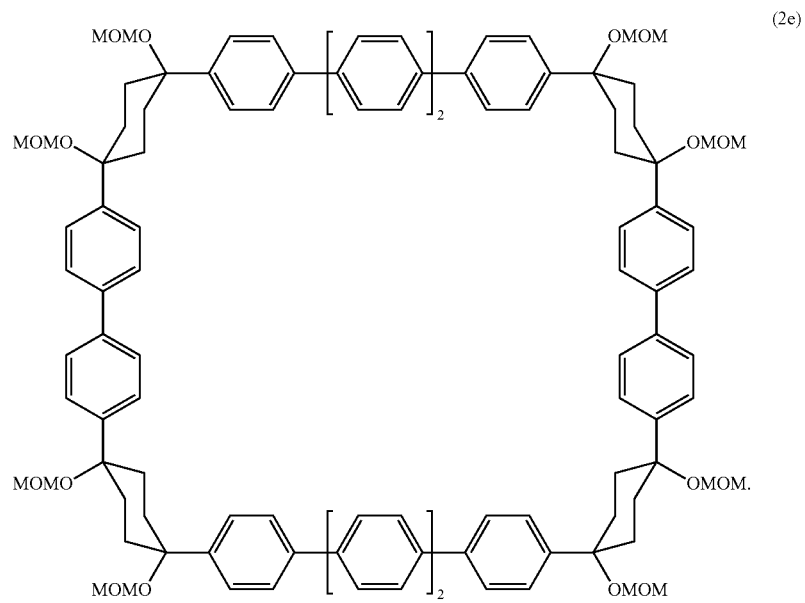

The yield of Cyclic Compound (2e) was 32%.

$^1$H NMR (270 MHz, CDCl$_3$) δ2.19 (brs, 16H), 2.40 (brs, 16H), 3.43 (s, 12H), 3.45 (s, 12H), 4.48 (s, 8H), 4.50 (s, 8H), 7.50-7.70 (m, 48H); $^{13}$C NMR (98.5 MHz, CDCl$_3$) δ33.1 (CH$_2$), 56.1 (CH$_2$), 78.2 (e), 92.3 (CH$_2$), 126.9 (CH), 127.4 (CH), 127.5 (CH), 139.6 (CH), 139.8 (4°); HRMS (FAB) m/z calcd for C$_{112}$H$_{120}$O$_{16}$Na [M$^+$Na]$^+$: 1743.8474, found 1743.8496.

Example 11

Production of Carbon Nanoring (1f) Made of Cycloparaphenylene Containing 16 Benzene Rings To a 20-mL Schlenk flask containing a stirring bar were added Cyclic Compound (2e) obtained in Example 10 (12.5 mg, 7.26 μmol), sodium hydrogen sulfate monohydrate (20.0 mg, 145 µmol), dry xylene (m-Xylene) (1.2 mL), and dry dimethylsulfoxide (DMSO) (1.2 mL). The resulting mixture was reacted at 160° C. for 48 hours while stirring. Subsequently, the mixture (reaction liquid) in the Schlenk flask was cooled to room temperature and extracted with CHCl$_3$. After the organic phase from the extraction was dried over Na$_2$SO$_4$, the solvent was distilled off under reduced pressure to yield a crude product. The crude product was purified by silica gel preparative thin layer chromatography (CH$_2$Cl$_2$/hexane) to yield a white solid (2.5 mg). This white solid was identified by nuclear magnetic resonance ($^1$H-NMR, $^{13}$C-NMR) analysis and mass spectrometry as [16] cycloparaphenylene (amorphous) containing 16 benzene rings, represented by the following General Formula (1f):

[Chem. 71]

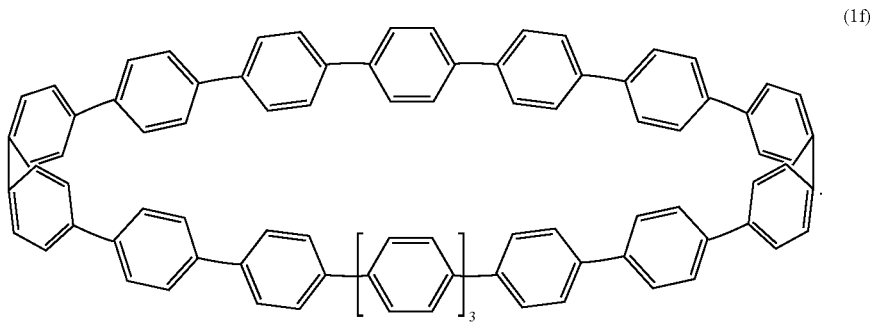

(1f)

The yield of [16] cycloparaphenylene was 28%.

$^1$H NMR (600 MHz, CDCl$_3$) δ7.68 (s, 64H); $^{13}$C NMR (98.5 MHz, CDCl$_3$) δ 127.3 (CH), 138.9 (4°); HRMS (MALDI-TOF) m/z calcd for C$_{96}$H$_{64}$ [M]$^+$: 1216.5008, found 121.

Example 12

Production of Cyclic Compound (2a) Containing 14 Organic Rings Including a Naphthylene Ring To a 50-mL round-bottom flask containing a stirring bar were added Compound (3a-1) obtained in Example 3 (20.0 mg, 20 µmol), Compound (4a) obtained in Synthesis Example 5 (29.4 mg, 28 µmol), [Pd(OAc)$_2$] (0.9 mg, 4.0 µmol), and X-Phos (2.0 mg, 4.2 µmol), and argon gas was introduced into the flask. Dry dioxane (1,4-dioxane) (10 mL) and a 10 M sodium hydroxide (NaOH) aqueous solution (10 µL, 0.10 mmol) were added thereto, and the resulting mixture was reacted at 80° C. for 24 hours while stirring. Thereafter, the mixture (reaction liquid) in the flask was cooled to room temperature and passed through silica gel. After the solvent was distilled off from the resulting filtrate under reduced pressure using an evaporator, the residue (concentrate) was purified by silica gel chromatography (CHCl$_3$/EtOAc=1/1) to yield a white solid (4.0 mg). This white solid was identified by nuclear magnetic resonance ($^1$H-NMR) analysis and mass spectrometry as a cyclic compound in which 14 organic rings including phenylene groups, a naphthylene group, and cyclohexylene derivative groups were continuously linked (hereinafter sometimes referred to as "Cyclic Compound (2a)"), the compound being represented by the following General Formula (2a):

[Chem. 72]

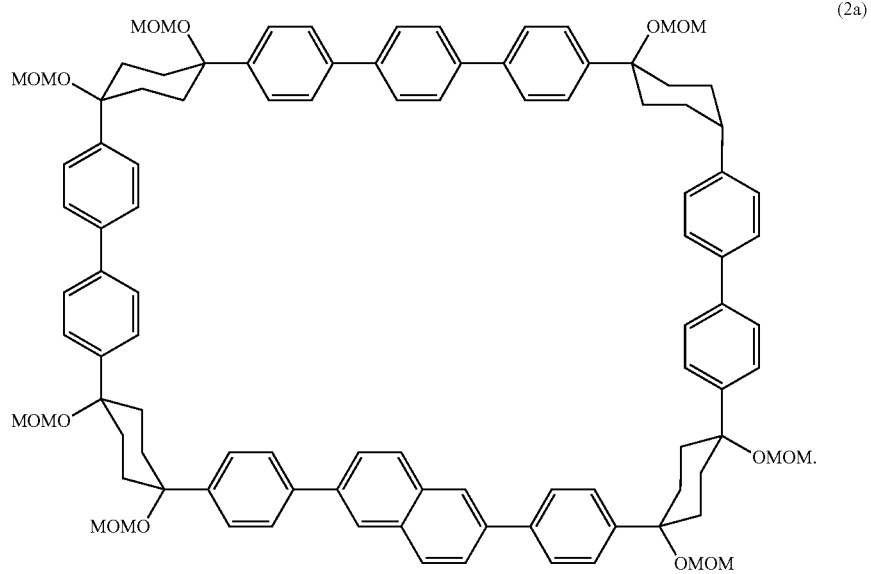

(2a)

The yield of Cyclic Compound (2a) was 12%.

$^1$H NMR (270 MHz, CDCl$_3$) δ2.14 (brs, 16H), 2.38 (brs, 16H), 3.43 (m, 24H), 4.48 (m, 16H), 7.60 (m, 38H), 7.91 (d, J=8.6 Hz, 2H), 8.01 (s, 2H). LRMS (FAB) m/z calcd for C$_{104}$H$_{114}$O$_{16}$[M]$^+$: 1619.8140, found 1620.

Example 13

Production of Compound (3a-1) (Part 2)

To a 100-mL round-bottom flask containing a stirring bar were added Compound (10b) obtained in Synthesis Example 2 (2.49 g, 4.84 mmol), Compound (11a) obtained in Synthesis Example 4 (190 mg, 500 μmol), Pd(PPh$_3$)$_4$ (15.0 mg, 13.0 μmol), sodium carbonate (Na$_2$CO$_3$) (268 mg, 2.53 mmol), tetra-n-butylammonium bromide (n-Bu$_4$NBr) (555 mg, 499 μmol), dry THF (20 mL), and argon-bubbled water (5 mL). The resulting mixture was reacted at 60° C. for 24 hours while stirring. Subsequently, the mixture (reaction liquid) in the flask was cooled to room temperature and filtered under reduced pressure. The residue (concentrate) was extracted with EtOAc, dried over Na$_2$SO$_4$, and filtered under reduced pressure. The crude product was purified by silica gel chromatography (hexane/EtOAc=8:1 to 2:1) to yield a white solid (359 mg). This white solid was identified by nuclear magnetic resonance ($^1$H-NMR, $^{13}$C-NMR) analysis and mass spectrometry as Compound (3a-1) represented by the following General Formula (3a-1):

[Chem. 73]

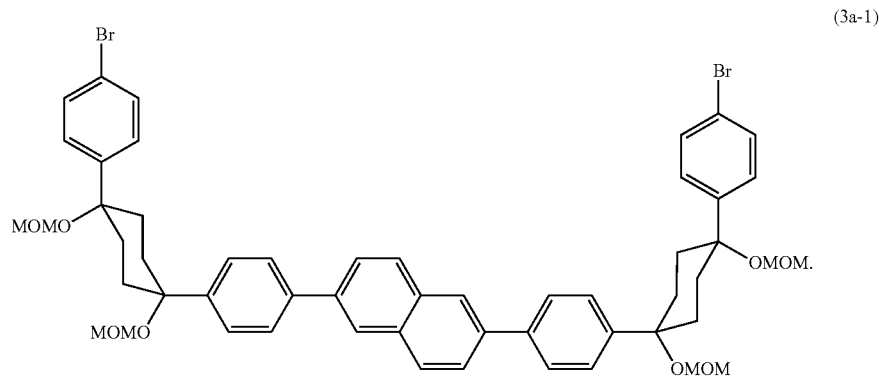

(3a-1)

The yield of Compound (3a-1) was 72%. Unreacted Compound (10b) (2.00 g) was also recovered through this purification process.

$^1$H NMR (400 MHz, CDCl$_3$) δ 2.12 (brs, 8H), 2.27-2.48 (brm, 8H), 3.42 (s, 6H), 3.44 (s, 6H), 4.44 (s, 4H), 4.50 (s, 4H), 7.33 (d, J=8 Hz, 4H), 7.45 (d, J=8 Hz, 4H), 7.55 (d, J=8 Hz, 4H), 7.70 (d, J=8 Hz, 4H), 7.75 (dd, J=8 Hz, 1 Hz, 4H), 7.94 (d, J=8 Hz, 2H), 8.04 (d, J=1 Hz, 2H); $^{13}$C NMR (100 MHz, CDCl$_3$) δ 33.0 (CH$_2$), 56.1 (CH$_3$), 77.2 (4°), 77.9 (4°), 78.1 (4°), 92.2 (CH$_2$), 92.3 (CH$_2$), 121.7 (4°), 126.9 (CH), 127.4 (CH), 128.7 (4°), 131.5 (CH), 139.5 (4°), 139.8 (4°); HRMS (FAB) m/z calcd for C$_{54}$H$_{58}$Br$_2$O$_8$Na [M+Na]$^+$: 1015.2396, found 1015.2394; mp: 193.6-194.4° C.

Example 14

Production of Cyclic Compound (2a) Containing 14 Organic Rings Including a Naphthylene Ring To a 50-mL Schlenk flask containing a stirring bar were added Compound (3a-1) obtained in Example 13 (40.1 mg, 40.3 μmol), Compound (4a) obtained in Synthesis Example 5 (50.2 mg, 48.3 μmol), Pd$_2$(dba)$_3$ (3.6 mg, 3.9 μmol), X-Phos (3.7 mg, 7.8 μmol), and K$_3$PO$_4$ (85.0 mg, 400 μmol), and the flask was evacuated and backfilled with argon gas three times. Then, argon-bubbled 1,4-dioxane (20 mL) and argon-bubbled water (80 μL) were added to the flask under a flow of argon. After stirring at 80° C. for 24 hours, the resulting mixture was filtered through a silica gel layer to remove the solvent (EtOAc). Thereafter, the solvent was distilled off under reduced pressure to obtain a crude product. The crude product was purified by gel permeation chromatography and preparative thin-layer chromatography (CHCl$_3$/EtOAc=1:1) to yield a white solid (22.6 mg). This white solid was identified by nuclear magnetic resonance ($^1$H-NMR, $^{13}$C-NMR) analysis and mass spectrometry as a cyclic compound (hereinafter sometimes referred to as "Cyclic Compound (2a)") represented by the following General Formula (2a):

[Chem. 74]

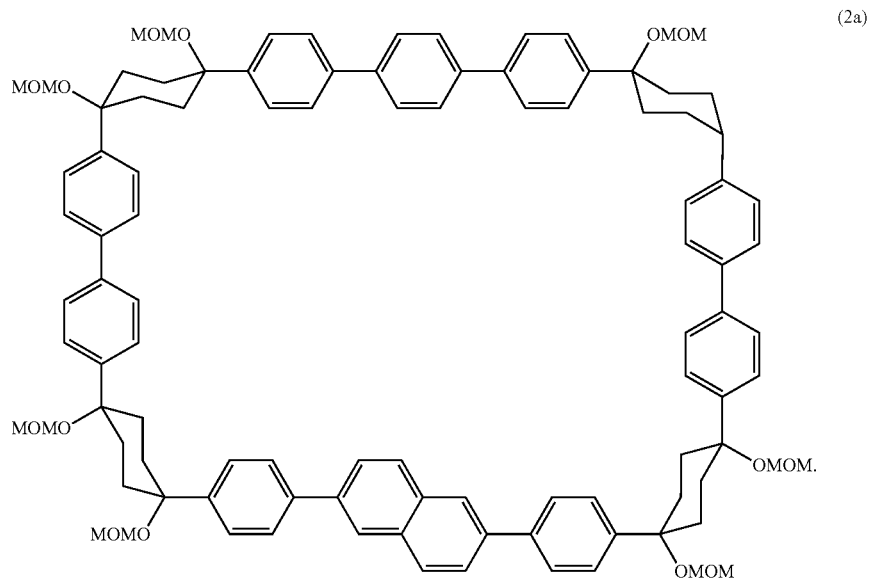

(2a)

The yield of Cyclic Compound (2a) was 35%.

$^1$H NMR (400 MHz, CDCl$_3$) δ 1.80-2.66 (brm, 32H), 3.42 (s, 6H), 3.44 (s, 18H), 4.45 (s, 4H), 4.46 (s, 4H), 4.49 (s, 4H), 4.53 (s, 4H), 7.40-7.66 (m, 32H), 7.69 (d, J=8 Hz, 4H), 7.73 (d, J=9 Hz, 2H), 7.92 (d, J=9 Hz, 2H), 8.02 (s, 2H); $^{13}$C NMR (100 MHz, CDCl$_3$) δ 33.0 (CH$_2$), 55.9 (CH$_3$), 56.1 (CH$_3$), 77.94 (4°), 78.00 (4°), 78.1 (4°), 78.2 (4°), 92.1 (CH$_2$), 92.2 (CH$_2$), 125.4 (CH), 125.8 (CH), 126.8 (CH), 127.2 (CH), 127.3 (CH), 128.3 (CH), 128.7 (CH), 137.9 (4°), 139.4 (4°) 139.5 (4°), 139.6 (4°) 139.7 (4°), 140.1 (4°) 141.6 (br, 4°); HRMS (FAB) m/z calcd for C$_{104}$H$_{114}$O$_{16}$Na [M+Na]$^+$: 1641.8005, found 1641.8009; mp: 235.0-240.0° C. (dec.).

Example 15

Production of Carbon Nanoring (1b) Made of 14 Organic Rings Including a Naphthylene Ring To a 20-mL Schlenk flask containing a stirring bar and a condenser were added Cyclic Compound (2a) obtained in Example 14 (16.2 mg, 10.0 µmol), sodium hydrogen sulfate monohydrate (NaHSO$_4$·H$_2$O) (27.2 mg, 197 µmol), dry DMSO (1 mL), and m-xylene (2.0 mL). The resulting mixture was heated at 150° C. for 24 hours while stirring under air atmosphere. The mixture was cooled to room temperature and filtered through a silica gel layer to remove the solvent (CHCl$_3$). Thereafter, the solvent was distilled off under reduced pressure to obtain a crude product. The crude product was purified by thin layer chromatography (CH$_2$Cl$_2$/hexane) to yield a light yellow solid (2.8 mg). This light yellow solid was identified by nuclear magnetic resonance ($^1$H-NMR, $^{13}$C-NMR) analysis and mass spectrometry as Carbon Nanoring (1b) made of 14 organic rings including a naphthylene ring, the carbon nanoring being represented by the following General Formula (1b):

The yield of this carbon nanoring was 25%.

$^1$H NMR (600 MHz, CDCl$_3$) δ 7.657 (brs, 44H), 7.670 (d, J=8 Hz, 4H), 7.74 (d, J=8 Hz, 4H), 7.77 (d, J=9 Hz, 2H), 7.87 (d, J=9 Hz, 2H), 8.01 (s, 2H); $^{13}$C NMR (150 MHz, CDCl$_3$) δ 125.5 (CH), 125.7 (CH), 127.3 (CH), 127.4 (CH), 127.5 (CH), 127.6 (CH), 128.7 (CH), 133.1 (4°), 137.3 (4°), 138.7 (4°), 138.78 (4°), 138.82 (4°), 138.84 (4°), 138.9 (4°), 139.1 (4°); HRMS (MALDI-TOF) m/z calcd for O$_{84}$H$_{56}$ [M]$^+$: 1114.4543, found 1114.4539.

Example 16

Production of Compound (3b-1)

To a 50-mL Schlenk flask containing a stirring bar were added Compound (4a) obtained in Synthesis Example 5 (103 mg, 99.1 µmol), 5,5'-dibromo-2,2'-bipyridine (315 mg, 1.00 mmol), (1,1'-bis(diphenylphosphino)ferrocene)dichloropalladium(II) (PdCl$_2$(dppf)) (7.4 mg, 10 µmol), sodium carbonate (Na$_2$CO$_3$) (53.9 mg, 509 µmol), and tetra-n-butylammonium bromide (n-Bu$_4$NBr) (32.7 mg, 101 µmol), and the flask was evacuated and backfilled with argon gas three times. Thereafter, dry toluene (5 mL) and degassed water (5 mL) were added thereto, and the mixture was stirred under reflux for 48 hours. Thereafter, the mixture was extracted with CH$_2$Cl$_2$, dried over Na$_2$SO$_4$, and filtered under reduced pressure. The crude product was purified by column chromatography (CHCl$_3$/MeOH=20:1) to yield a white solid (73.4 mg). This white solid was identified by nuclear magnetic resonance ($^1$H-NMR) analysis and mass spectrometry as a compound (hereinafter sometimes referred to as "Compound (3b-1)") represented by the following General Formula (3b-1):

[Chem. 75]

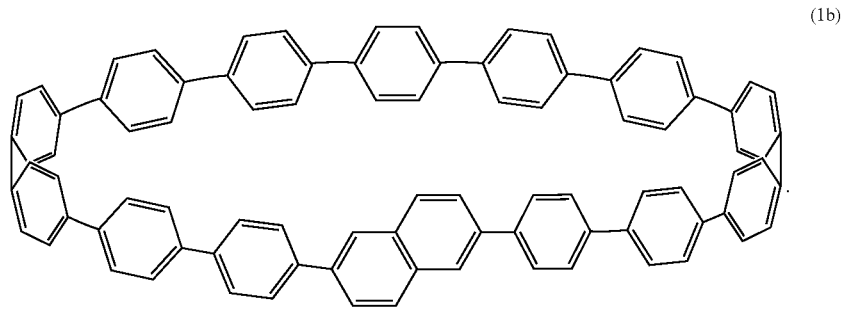

(1b)

(3b-1)

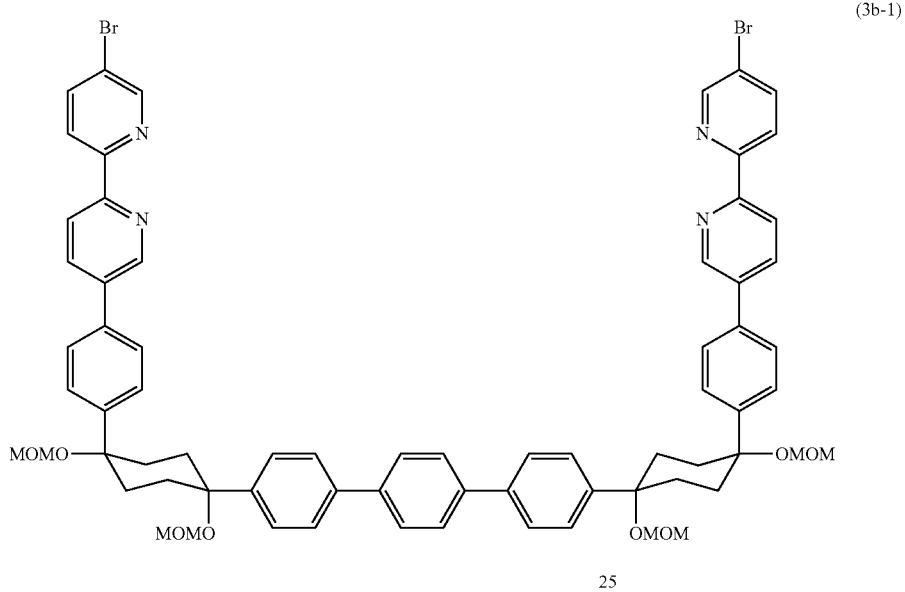

The yield of this compound was 59%.

$^1$H NMR (400 MHz, CDCl$_3$) 2.05-2.50 (brm, 16H), 3.45 (d, J=3 Hz, 12H), 4.50 (d, J=5 Hz, 8H), 7.51-7.66 (brm, 20H), 7.94 (dd, J=9 Hz, 2H), 7.99 (dd, J=8 Hz, 2H), 8.34 (d, J=8 Hz, 2H), 8.43 (d, J=9 Hz, 2H), 8.73 (s, 2H), 8.88 (s, 2H); MS (FAB) m/z calcd for C$_{70}$H$_{69}$Br$_2$N$_4$O$_8$[M$^+$H]$^+$: 1251.3482, found 1254.

Example 17

Production of Cyclic Compound (2b) Containing 18 Organic Rings Including Hetero Rings To a 50-mL Schlenk flask containing a stirring bar were added Compound (4a) obtained in Synthesis Example 5 (19.4 mg, 19 μmol), Compound (3b-1) obtained in Example 16 (18.6 mg, 14.9 μmol), (1,1'-bis(diphenylphosphino)ferrocene)dichloropalladium(II) (PdCl$_2$(dppf)) (1.4 mg, 1.9 μmol), sodium carbonate (Na$_2$CO$_3$) (8.0 mg, 76 μmol), and tetra-n-butylammonium bromide (n-Bu$_4$NBr) (5.2 mg, 16 μmol), and the flask was evacuated and backfilled with argon gas three times. Thereafter, dry toluene (7.5 mL) and degassed water (7.5 mL) were added thereto, and the mixture was stirred under reflux for 41 hours. Thereafter, the mixture was extracted with CH$_2$Cl$_2$, dried over Na$_2$SO$_4$, and filtered under reduced pressure. The crude product was purified by preparative thin-layer chromatography (CHCl$_3$) to yield a product (9.5 mg). The yielded product was identified by nuclear magnetic resonance ($^1$H-NMR) analysis and mass spectrometry as a cyclic compound (hereinafter sometimes referred to as "Cyclic Compound (2b)") represented by the following General Formula (2b):

(2b)

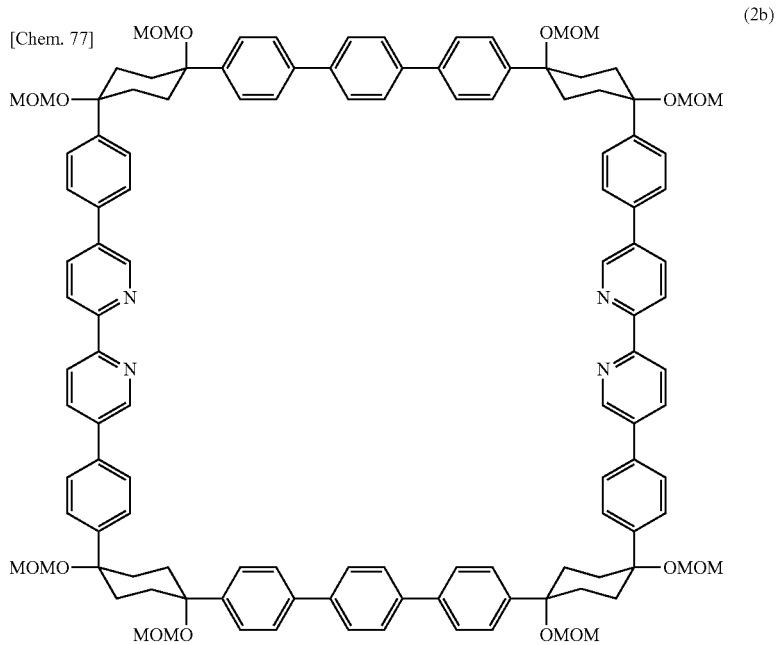

The yield of this Cyclic Compound (2b) was 34%.

$^1$H NMR (400 MHz, CDCl$_3$) δ 1.93-2.53 (brm, 32H), 3.45 (d, J=2 Hz, 24H), 4.51 (d, J=5 Hz, 16H), 7.48-7.66 (brm, 40H), 8.01 (dd, J=4 Hz, 4H), 8.48 (d, J=4 Hz, 4H), 8.91 (d, J=1 Hz, 4H); MS (FAB) m/z calcd for C$_{120}$H$_{125}$N$_4$O$_{16}$ [M$^+$H]$^+$: 1877.9091, found 1878

Example 18

Production of Carbon Nanoring (1c) Made of 18 Organic Rings Including Hetero Rings To a 50-mL Schlenk flask containing a stirring bar were added Cyclic Compound (2b) obtained in Example 17 (9.5 mg, 5.1 μmol), sodium hydrogen sulfate monohydrate (NaHSO$_4$·H$_2$O) (15.5 mg, 112 μmol), o-chloranil (6.5 mg, 36 μmol), dry m-xylene (1.0 mL), and DMSO (0.3 mL). The resulting mixture was stirred under reflux for 46 hours, and filtered under reduced pressure. The crude product was purified by preparative thin-layer chromatography (CHCl$_3$/MeOH=20:1) to yield a product (2.8 mg). This product was identified by nuclear magnetic resonance ($^1$H-NMR) analysis and mass spectrometry as cyclo[14] paraphenylene[4] pyridyridene (CPPy) represented by the following General Formula (1c):

[Chem. 78]

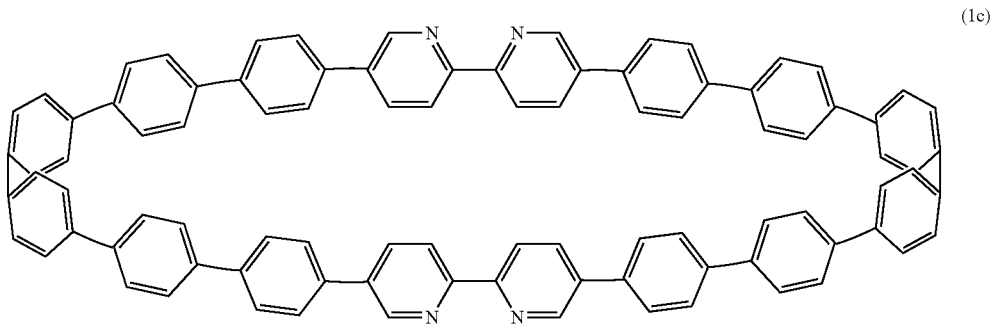

(1c)

The yield of this compound was 40%.

$^1$H NMR (400 MHz, CDCl$_3$) δ 7.71 (brs, 48H), 7.73 (d, 8H), 8.05 (dd, J=4 Hz, 4H), 8.45 (d, J=5 Hz, 4H), 8.97 (d, J=2 Hz, 4H), HRMS (MALDI-TOF) m/z calcd for C$_{104}$H$_{69}$N$_4$ [M$^+$H]$^+$: 1373.5522, found 1374.258.

Reference Example

Optical Properties of [14]-[16] Cycloparaphenylenes

Regarding [14]-[16] cycloparaphenylenes (CPPs) obtained in the Examples above, each solid sample (amorphous) was weighed to three significant figures, and using a 50-mL volumetric flask, each solution diluted with chloroform was prepared. Table 1 shows the concentration of each of the resulting diluted solutions of [14]-[16] cycloparaphenylenes.

The optical property (fluorescence spectrum) of each of the diluted solutions obtained above was measured under the following conditions (the devices and equipment used). Table 1 also shows the measurement results. The excitation wavelength used in measuring the fluorescence spectrum was a maximum absorption wavelength.

UV-visible-near IR spectrophotometer: UV-3600, produced by Shimadzu Corp

Spectrophotofluorometer: F-4500, produced by Hitachi, Ltd.

Absolute PL quantum yield measurement system: C9920-02 with 1-cm quartz cell, produced by Hamamatsu Photonics K.K.

TABLE 1

| Concentration of Solution (M) | Maximum Absorption Wavelength (nm) | Longest Absorption Wavelength (nm) | Fluorescence Peak Top 1 (nm) | Fluorescence Peak Top 2 (nm) | Absolute Quantum Yield |
|---|---|---|---|---|---|
| [14]CPP $3.9 \times 10^{-6}$ | 338.0 | 368.5 | 421.4 | 442.8 | 0.89 |
| [15]CPP $1.5 \times 10^{-6}$ | 339.0 | 370.0 | 417.2 | 440.6 | 0.90 |
| [16]CPP $2.4 \times 10^{-6}$ | 338.5 | 364.0 | 415.8 | 437.8 | 0.88 |

Referring to the measurement results of the optical property above, it is understood that [14]-[16] cycloparaphenylenes are materials having high fluorescence efficiency of blue luminescence.

The invention claimed is:

1. A carbon nanoring represented by General Formula (1):

[Chem. 7]

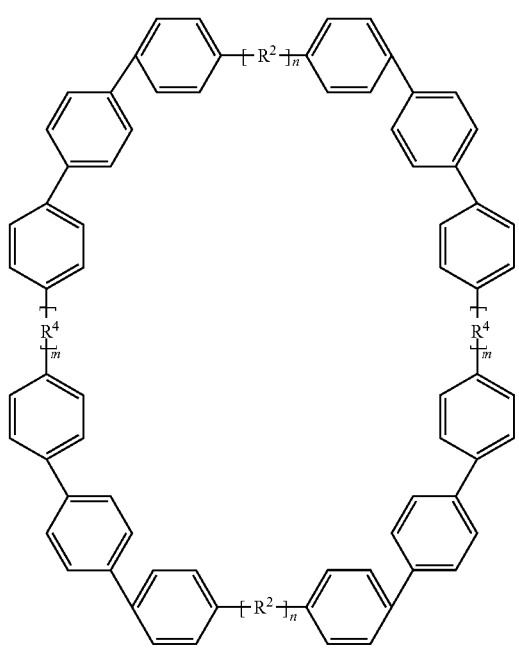

(1)

wherein $R^2$ is the same or different, and each represents a bivalent aromatic hydrocarbon group, a bivalent alicyclic hydrocarbon group, or a bivalent heterocyclic group; $R^4$ is the same or different, and each represents a bivalent aromatic hydrocarbon group, a bivalent alicyclic hydrocarbon group, or a bivalent heterocyclic group; n is the same or different, and each represents an integer of 1 or more; and m is the same or different, and each represents an integer of 0 or more, wherein the total number of phenylene, $R^2$, and $R^4$ is 13, 19 or 20.

2. The carbon nanoring according to claim 1, wherein $R^2$ and $R^4$ are the same or different, and each represents a group containing a bivalent 6-membered aromatic ring or a bivalent 6-membered heterocyclic aromatic ring, and is bonded at the para-positions.

3. The carbon nanoring according to claim 1, wherein —$(R^2)_n$— is the same or different, and is represented by General Formula (5):

[Chem. 8]

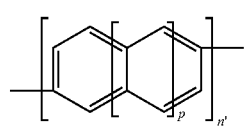

(5)

wherein n' is 1 or 2; and p is 0, 1, 2 or 3.

4. The carbon nanoring according to claim 1, wherein —$(R^4)_m$— is the same or different, and is represented by General Formula (7):

[Chem. 9]

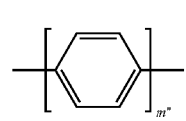

(7)

wherein m'' is 1, 2, or 3, or General Formula (8):

[Chem. 10]

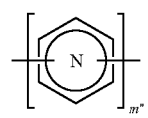

(8)

wherein m'' is 1, 2 or 3; and a ring of a repeating unit is a 6-membered heterocyclic aromatic ring having nitrogen.

5. The carbon nanoring according to claim 1, wherein $R^2$ and $R^4$ are all phenylenes.

6. The carbon nanoring according to claim 1, wherein n is 1 or 2, and m is an integer of 0 to 3.

7. A carbon nanoring represented by General Formula (1):

[Chem. 20]

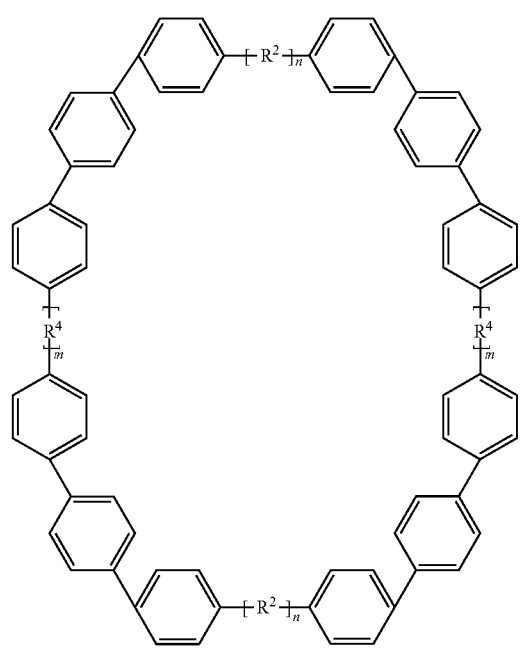

(1)

wherein $R^2$ is the same or different, and each represents a bivalent aromatic hydrocarbon group, a bivalent alicyclic hydrocarbon group, or a bivalent heterocyclic group; $R^4$ is the same or different, and each represents a bivalent aromatic hydrocarbon group, a bivalent alicyclic hydrocarbon group, or a bivalent heterocyclic group; n is the same or different, and each represents an integer of 1 or more; and m is the same or different, and each represents an integer of 0 or more, wherein at least one $-(R^2)_n-$ is represented by General Formula (5):

[Chem. 21]

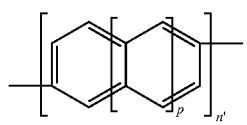

(5)

wherein n' is 1 or 2; and p is 1, 2 or 3.

8. A carbon nanoring represented by General Formula (1):

[Chem. 22]

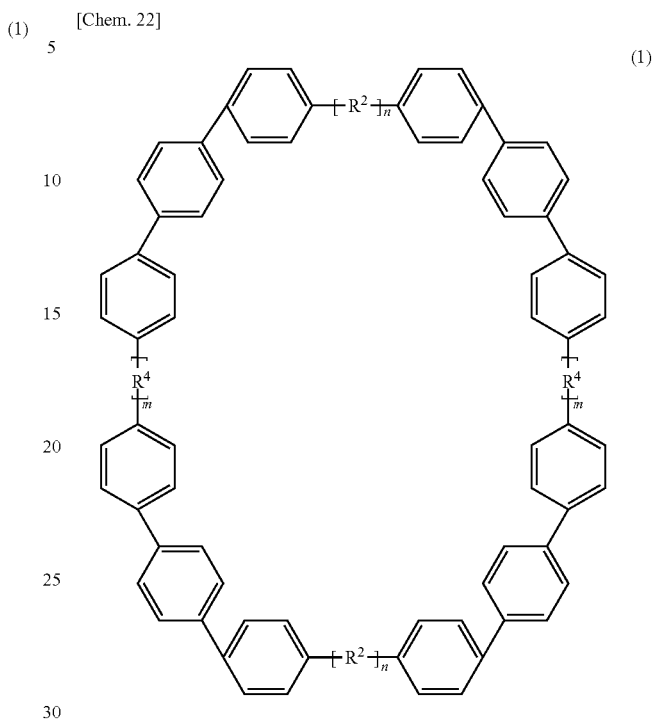

(1)

wherein $R^2$ is the same or different, and each represents a bivalent aromatic hydrocarbon group, a bivalent alicyclic hydrocarbon group, or a bivalent heterocyclic group; $R^4$ is the same or different, and each represents a bivalent aromatic hydrocarbon group, a bivalent alicyclic hydrocarbon group, or a bivalent heterocyclic group; n is the same or different, and each represents an integer of 1 or more; and m is the same or different, and each represents an integer of 0 or more, wherein at least one $-(R^4)_m-$ is represented by General Formula (8):

[Chem. 23]

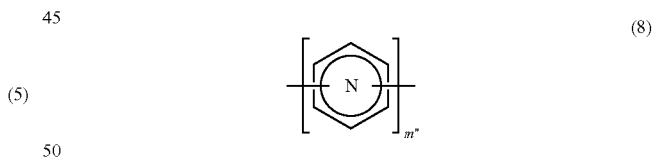

(8)

wherein m" is 1, 2 or 3; and a ring of a repeating unit is a 6-membered heterocyclic aromatic ring having nitrogen.

* * * * *